United States Patent [19]

Bowman et al.

[11] Patent Number: 5,352,795
[45] Date of Patent: Oct. 4, 1994

[54] ALPHA-HETEROCYCLE SUBSTITUTED TOLUNITRILES

[75] Inventors: Robert M. Bowman, Summit; Leslie J. Browne, Morristown, both of N.J.

[73] Assignee: Ciba-Geigy Corporation, Ardsley, N.Y.

[21] Appl. No.: 882,188

[22] Filed: May 11, 1992

Related U.S. Application Data

[60] Division of Ser. No. 628,732, Dec. 17, 1990, Pat. No. 5,112,845, which is a continuation-in-part of Ser. No. 240,862, Sep. 6, 1988, Pat. No. 4,978,672, which is a continuation-in-part of Ser. No. 164,696, Mar. 7, 1988, Pat. No. 4,937,250, which is a division of Ser. No. 837,489, Mar. 7, 1986, Pat. No. 4,749,713.

[51] Int. Cl.$^5$ ............................................. C07D 249/08
[52] U.S. Cl. .................................................. 548/262.2
[58] Field of Search ........................... 548/262.2, 335; 546/330

[56] References Cited

U.S. PATENT DOCUMENTS

| | | | |
|---|---|---|---|
| 4,749,713 | 6/1988 | Bowmann et al. | 514/341 |
| 4,755,526 | 7/1988 | Hirsch et al. | 514/399 |
| 4,757,076 | 7/1988 | Hirsch et al. | 514/277 |
| 4,801,594 | 1/1989 | Hirsch et al. | 514/340 |
| 4,866,086 | 9/1989 | Boyle et al. | 514/383 |
| 4,916,144 | 4/1990 | Strehike et al. | 514/326 |
| 4,937,250 | 6/1990 | Bowmann et al. | 514/341 |
| 4,978,672 | 12/1990 | Bowmann et al. | 514/383 |
| 5,021,434 | 6/1991 | Strehike et al. | 514/341 |

FOREIGN PATENT DOCUMENTS 354689 2/1990 European Pat. Off. .
411735 2/1991 European Pat. Off. .

OTHER PUBLICATIONS

Derwent Abstract 91-038641 (of EP411735 in English), 1991.
J. Med. Chem. vol. 30, 1359 (1987).
Advanced Organic Chemistry, Third Edition, (1985) pp. 411–415 & pp. 596–597, by Jerry March.
Advanced Organic Chemistry, Fourth Edition, (1992) pp. 464–468 & pp. 662–664, by Jerry March.
J. Org. Chem. 31, 2319 (1966).
J. Chem. Soc. Perkin Trans. I, 1988, pp. 1331–1335.
Blicke Thiophene and its Derivatives. p. 29 1952.
Buehler et al. 1977. Survey of Org. Syn. pp. 37–39.
March Advanced Organic Chem. pp. 604–605 1968.

*Primary Examiner*—Jane T. Fan
*Attorney, Agent, or Firm*—Norbert Gruenfeld

[57] ABSTRACT

The invention is concerned with aromatase inhibiting compounds of formula I

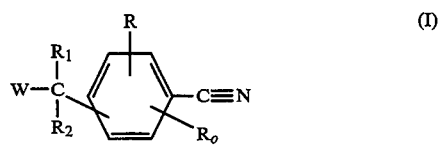

wherein R and Ro represent hydrogen or lower alkyl; or R and Ro located on adjacent carbon atoms and together when combined with the benzene ring to which they are attached form a naphthalene or tetrahydronaphthalene ring; $R_1$ and $R_2$ independently represent hydrogen, lower alkyl, (lower alkyl, aryl or aryl-lower alkyl)-thio, lower alkenyl, aryl, aryl-lower alkyl, $C_3$–$C_6$-cycloalkyl, or $C_3$–$C_6$-cycloalkyl-lower alkyl; or $R_1$ and $R_2$ combined represent lower alkylidene, mono- or di-aryl-lower alkylidene; $R_1$ and $R_2$ combined also represent $C_4$–$C_6$-straight chain alkylene, lower alkyl-substituted straight chain alkylene or ortho-phenylene bridged-$C_2$–$C_4$-straight chain alkylene, each forming with the carbon atom attached thereto a corresponding optionally substituted or benzo-fused 5, 6 or 7-membered ring; W represents 1-imidazolyl, 1-(1,2,4- or 1,3,4)-triazolyl or 3-pyridyl; or W represents 1-imidazolyl, 1-( 1,2,4 or 1,3,4)-triazolyl or 3-pyridyl substituted by lower alkyl; and pharmaceutically acceptable salts thereof.

4 Claims, No Drawings

ALPHA-HETEROCYCLE SUBSTITUTED TOLUNITRILES

CROSS REFERENCE TO RELATED APPLICATIONS

This application is a divisional application of application Ser. No. 628,732 filed Dec. 17, 1990, now U.S. Pat. No. 5,112,845, which is a continuation-in-part application of application Ser. No. 240,862, filed Sep. 6, 1988, now U.S. Pat. No. 4,978,672, which is a continuation-in-pan application of application Ser. No. 164,696, filed Mar. 7, 1988, now U.S. Pat. No. 4,937,250, which is a divisional application of application Ser. No. 837,489 filed Mar. 7, 1986, now U.S. Pat. No. 4,749,713.

SUMMARY OF THE INVENTION

The invention relates to certain heterocycle-substituted tolunitriles and derivatives described herein having valuable pharmacological properties, particularly as aromatase inhibitors, to pharmaceutical compositions containing same, to the use of such heterocycle-substituted tolunitriles for inhibiting aromatase activity and suppressing estrogen synthesis in mammals and for treating conditions responsive to aromatase inhibition and to inhibition of estrogen biosynthesis in mammals.

The compounds of the invention are active and useful as aromatase inhibitors in mammals. The compounds of the invention are therefore also useful, when administered alone or in combination to mammals as inhibitors of estrogen synthesis and for the treatment and amelioration of estrogen dependent conditions, e.g. gynecomastia, mammary and endometrial tumors, endometriosis and premature labor; they are further useful as antifertility agents.

Furthermore, the compounds of the invention are useful for delaying proestrus and estrus and preventing estrus in animals.

DETAILED DESCRIPTION OF THE INVENTION

Particularly the invention relates to the aromatase inhibiting compounds of formula I

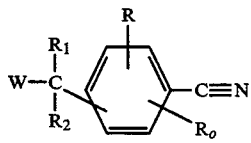

(I)

wherein R and Ro represent hydrogen or lower alkyl; or R and Ro located on adjacent carbon atoms and together when combined with the benzene ring to which they are attached form a naphthalene or tetrahydronaphthalene ring; $R_1$ and $R_2$ independently represent hydrogen, lower alkyl, (lower alkyl, aryl or aryl-lower alkyl)-thio, lower alkenyl, aryl, aryl-lower alkyl, $C_3$–$C_6$-cycloalkyl, or $C_3$–$C_6$-cycloalkyl-lower alkyl; or $R_1$ and $R_2$ combined represent lower alkylidene, mono- or di-aryl-lower alkylidene; $R_1$ and $R_2$ combined also represent $C_4$–$C_6$-straight chain alkylene, lower alkyl-substituted straight chain alkylene or ortho-phenylene bridged-$C_2$–$C_4$-straight chain alkylene, each forming with the carbon atom attached thereto a corresponding optionally substituted or benzo-fused 5, 6 or 7-membered ring; W represents 1-imidazolyl, 1-(1,2,4- or 1,3,4)-triazolyl or 3-pyridyl; or W represents 1-imidazolyl, 1-(1,2,4 or 1,3,4)-triazolyl or 3-pyridyl substituted by lower alkyl; and pharmaceutically acceptable salts thereof.

A specific embodiment of the invention relates to the compounds of formula I wherein W represents 1-imidazolyl or 1-imidazolyl substituted by lower alkyl; another embodiment relates to the compounds of formula I wherein W represents 1-(1,2,4- or 1,3,4-)-triazolyl or 1-(1,2,4- or 1,3,4-)-triazolyl substituted by lower alkyl; a further embodiment relates to the compounds of formula I wherein W represents 3-pyridyl or 3-pyridyl substituted by lower alkyl. Further particular embodiments relate to compounds of formula I wherein R and Ro represent hydrogen or lower alkyl; also those wherein R and Ro together with the benzene ring to which they are attached form a naphthalene or tetrahydronaphthalene ring.

Preferred are the compounds of formula I wherein the

grouping is attached para to the cyano group.

Preferred are the said compounds of formula I wherein R and Ro represent hydrogen or lower alkyl; or R and Ro located on adjacent carbon atoms and together when combined with the benzene ring to which they are attached form a naphthalene or tetrahydronaphthalene ring; $R_1$ represents hydrogen, lower alkyl, aryl, aryl-lower alkyl or lower alkenyl; $R_2$ represents hydrogen, lower alkyl, aryl, aryl-lower alkyl, (lower alkyl, aryl or aryl-lower alkyl)-thio or lower alkenyl; or $R_1$ and $R_2$ combined represent lower alkylidene or $C_4$–$C_6$-alkylene; W has meaning given above; and aryl within the above definitions represents phenyl or phenyl substituted by one or two substituents selected from lower alkyl, lower alkoxy, hydroxy, acyloxy, nitro, amino, halogen, trifluoromethyl, cyano, carboxy, carboxy functionalized in form of a pharmaceutically acceptable ester or amide, lower alkanoyl, aroyl, lower alkylsulfonyl, sulfamoyl, N-lower alkylsulfamoyl or N,N-di-lower alkylsulfamoyl; or aryl within the above definitions also represents a heterocyclic aromatic radical selected from thienyl, indolyl, pyridyl and furyl, or a said heterocyclic radical monosubstituted by lower alkyl, lower alkoxy, cyano or halogen; and pharmaceutically acceptable salts thereof.

An embodiment relates to the compounds of formula I wherein R and Ro represent hydrogen or lower alkyl; or R and Ro located on adjacent carbon atoms and together when combined with the benzene ring to which they are attached form a naphthalene or tetrahydronaphthalene ring; $R_1$ represents hydrogen; $R_2$ represents hydrogen, lower alkyl, lower alkenyl, aryl, aryl-lower alkyl, $C_3$–$C_6$-cycloalkyl, or $C_3$–$C_6$-cycloalkyl-lower alkyl; or $R_1$ and $R_2$ combined represent lower alkylidene, or mono- or di-aryl-lower alkylidene; $R_1$ and $R_2$ combined also represent $C_4$–$C_6$-straight chain alkylene, lower alkyl-substituted straight chain alkylene or ortho phenylene bridged-$C_2$–$C_4$ straight chain alkylene to form with the carbon atom attached thereto a corresponding optionally substituted or benzo-fused 5, 6 or 7-membered ring; W represents 1-imidazolyl, 1-(1,2,4-or 1,3,4)-triazolyl or 3-pyridyl; or W represents 1-imidazolyl, 1-(1,2,4 or 1,3,4)-triazolyl or 3-pyridyl substituted by lower alkyl; or a pharmaceutically acceptable salt thereof.

Another embodiment relates to the compounds of formula I wherein R and Ro represent hydrogen or lower alkyl; or R and Ro located on adjacent carbon atoms and together when combined with the benzene ring to which they are attached form a naphthalene or tetrahydronaphthalene ring; $R_1$ represents hydrogen; $R_2$ represents hydrogen, lower alkyl, aryl, aryl-lower alkyl, or lower alkenyl; or $R_1$ and $R_2$ combined represent lower alkylidene or $C_4-C_6$-alkylene; W represents 1-imidazolyl or 1-imidazolyl sustituted by lower alkyl; and aryl within the above definitions represents phenyl or phenyl substituted by one or two substituents selected from lower alkyl, lower alkoxy, hydroxy, acyloxy, nitro, amino, halogen, trifluoromethyl, cyano, carboxy, carboxy functionalized in form of a pharmaceutically acceptable ester or amide, lower alkanoyl, aroyl, lower alkylsulfonyl, sulfamoyl, N-lower alkylsulfamoyl or N,N-di-lower alkylsulfamoyl; or aryl within the above definitions also represents a heterocyclic aromatic radical selected from thienyl, indolyl, pyridyl and furyl, or a said heterocyclic radical monosubstituted by lower alkyl, lower alkoxy, cyano or halogen; or a pharmaceutically acceptable salt thereof.

Particularly preferred are the above compounds of formula I wherein $R_1$ represents hydrogen; and W, R, Ro, $R_2$ as well as $R_1$ and $R_2$ combined have meaning as defined above.

Further preferred are the compounds of formula II

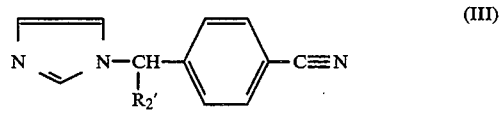

wherein $R_1'$ represents hydrogen; $R_2'$ represents hydrogen, lower alkyl, phenyl, pyridyl, thienyl or benzyl; or $R_2'$ represents phenyl or benzyl, each monosubstituted on the phenyl ring by cyano, lower alkyl, lower alkoxy, hydroxy, lower alkanoyloxy, aroyloxy, nitro, halogen, trifluoromethyl, lower alkanoyl, aroyl, lower alkylsulfonyl, carbamoyl, N-mono-or N,N-di-lower alkylcarbamoyl, sulfamoyl, N-mono- or N,N-di-lower alkylsulfamoyl; or $R_1'$ and $R_2'$ combined represent together lower alkylidene, benzylidene or diphenylmethylidene; or $R_1'$ and $R_2'$ combined represent together $C_4-C_6$-straight chain alkylene; $R_3$ represents hydrogen or lower alkyl; and pharmaceutically acceptable salts thereof.

Particularly preferred are the compounds of formula II wherein $R_1'$ represents hydrogen; $R_2'$ represents hydrogen, lower alkyl, pyridyl, benzyl or phenyl; or $R_2'$ represents benzyl or phenyl, each monosubstituted on phenyl by cyano, lower alkyl, lower alkoxy, hydroxy, lower alkanoyloxy, halogen, nitro, trifluoromethyl, lower alkanoyl, aroyl, lower alkylsulfonyl, carbamoyl, N-mono or N,N-di-lower alkylcarbamoyl, sulfamoyl, N-mono- or N,N-di-lower alkylsulfamoyl; $R_3$ represents hydrogen or lower alkyl; and pharmaceutically acceptable salts thereof.

Preferred in turn are the compounds of formula II wherein $R_1'$ represents hydrogen; $R_2'$ represents hydrogen, lower alkyl, benzyl, phenyl, or 3- or 4-pyridyl; or $R_2'$ represents phenyl or benzyl, each monosubstituted on phenyl by cyano, halogen, lower alkoxy, lower alkyl or trifluoromethyl; $R_3$ represents hydrogen or lower alkyl at the 4 or 5 position; and pharmaceutically acceptable salts thereof.

Particularly preferred are the compounds of formula II wherein $R_2'$ represents unsubstituted or monosubstituted phenyl or benzyl, or pyridyl, as defined hereinabove.

Most preferred are the compounds of formula III

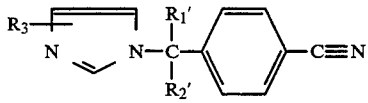

wherein $R_2'$ represents 3-pyridyl, p-cyanobenzyl or p-cyanophenyl; and pharmaceutically acceptable salts thereof.

A particular embodiment of the invention relates to the compounds of formula I wherein R and Ro are located on adjacent carbon atoms and together when combined with the benzene ring to which they are attached form a naphthalene or tetrahydronaphthalene ring.

A preferred embodiment thereof relates to the naphthonitriles of formula IV

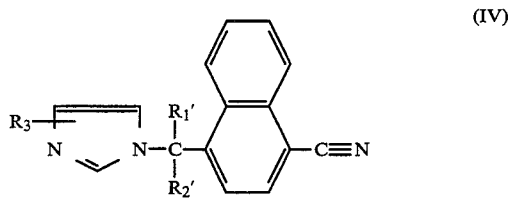

wherein $R_1'$ represents hydrogen; $R_2'$ represents hydrogen, lower alkyl, phenyl, lower alkylthio, phenyl-lower alkylthio, phenylthio, pyridyl, thienyl or benzyl; or $R_2'$ represents phenyl, phenyl-lower alkylthio, phenylthio or benzyl, each monosubstituted on the phenyl ring by cyano, lower alkyl, lower alkoxy, hydroxy, lower alkanoyloxy, aroyloxy, nitro, halogen, trifluoromethyl, lower alkanoyl, aroyl, lower alkylsulfonyl, carbamoyl, N-mono-or N,N-di-lower alkylcarbamoyl, sulfamoyl, N-mono- or N,N-di-lower alkylsulfamoyl; or $R_1'$ and $R_2'$ combined represent together lower alkylidene, benzylidene, diphenylmethylidene; or $R_1'$ and $R_2'$ combined represent together $C_4-C_6$ straight chain alkylene; $R_3$ represents hydrogen or lower alkyl; and pharmaceutically acceptable salts thereof.

Particularly preferred are the compounds of formula IV wherein $R_1'$ represents hydrogen; $R_2'$ represents hydrogen, lower alkyl, pyridyl; or $R_2'$ represents benzyl or phenyl, each unsubstituted or monosubstituted on phenyl by cyano, lower alkyl, lower alkoxy, hydroxy, lower alkanoyloxy, halogen, nitro, trifluoromethyl, lower alkanoyl, aroyl, lower alkylsulfonyl, carbamoyl, N-mono- or N,N-di-lower alkylcarbamoyl, sulfamoyl, N-mono or N,N-di-lower alkylsulfamoyl; $R_3$ represents hydrogen or lower alkyl; and pharmaceutically acceptable salts thereof.

Preferred in turn are the compounds of formula IV wherein $R_1'$ represents hydrogen; $R_2'$ represents hydrogen, lower alkyl, benzyl, phenyl, or 3 or 4-pyridyl; or $R_2'$ represents phenyl or benzyl, each monosubstituted on phenyl by cyano, halogen, lower alkoxy, lower alkyl or trifluoromethyl; $R_3$ represents hydrogen or lower alkyl at the 4 or 5 position; and pharmaceutically acceptable salts thereof.

Most preferred are the compounds of formula IV wherein $R_1'$ and $R_3$ represent hydrogen; $R_2'$ represents 3-pyridyl, p-cyanobenzyl or p-cyanophenyl; and pharmaceutically acceptable salts thereof.

Another specific preferred embodiment of the invention relates to compounds of formula I wherein W represents 1-(1,2,4)-triazolyl or 1-(1,2,4)-triazolyl substituted by lower alkyl, namely the compounds of formula V

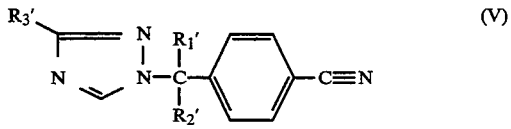

wherein $R_1'$ represents hydrogen; $R_2'$ represents hydrogen, lower alkyl, phenyl, pyridyl, thienyl or benzyl; or $R_2'$ represents phenyl or benzyl, each monosubstituted on the phenyl ring by cyano, lower alkyl, lower alkoxy, hydroxy, lower alkanoyloxy, aroyloxy, nitro, halogen, trifluoromethyl, lower alkanoyl, aroyl, lower alkylsulfonyl, carbamoyl, N-mono- or N,N-di-lower alkylcarbamoyl, sulfamoyl, N-mono- or N,N-di-lower alkylsulfamoyl; or $R_1'$ and $R_2'$ combined represent together lower alkylidene, benzylidene or diphenylmethylidene; or $R_1'$ and $R_2'$ combined represent together $C_4$-$C_6$ straight chain alkylene; $R_3'$ represents hydrogen or lower alkyl; and pharmaceutically acceptable salts thereof.

Particularly preferred are the compounds of formula V wherein $R_1'$ represents hydrogen; $R_2'$ represents hydrogen, lower alkyl, pyridyl; or $R_2'$ represents benzyl or phenyl, each unsubstituted or monosubstituted on phenyl by cyano, lower alkyl, lower alkoxy, hydroxy, lower alkanoyloxy, halogen, nitro, trifluoromethyl, lower alkanoyl, aroyl, lower alkylsulfonyl, carbamoyl, N-mono- or N,N-di-lower alkylcarbamoyl, sulfamoyl, N-mono- or N,N-di-lower alkylsulfamoyl; $R_3'$ represents hydrogen or lower alkyl; and pharmaceutically acceptable salts thereof.

Preferred in turn are the compounds of formula V wherein $R_1'$ represents hydrogen; $R_2'$ represents hydrogen, lower alkyl, benzyl, phenyl, or 3- or 4-pyridyl; or $R_2'$ represents phenyl or benzyl, each monosubstituted on phenyl by cyano, halogen, lower alkoxy, lower alkyl or trifluoromethyl; $R_3$ ' represents hydrogen or lower alkyl; and pharmaceutically acceptable salts thereof.

Most preferred are the compounds of formula V wherein $R_1'$ and $R_3'$ represent hydrogen; $R_2'$ represents 3-pyridyl, p-cyanobenzyl or p-cyanophenyl; and pharmaceutically acceptable salts thereof.

A further specific embodiment of the invention relates to compounds of the formula I wherein W represents a 3-pyridyl group, particularly the compounds of formula VI

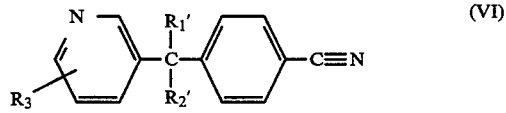

wherein $R_1'$ represents hydrogen; $R_2'$ represents hydrogen, lower alkyl, phenyl, lower alkylthio, phenyl-lower alkylthio, phenylthio, pyridyl, thienyl, benzyl; or $R_2'$ represents phenyl, phenyl-lower alkylthio, phenylthio or benzyl each monosubstituted on the phenyl ring by cyano, lower alkyl, lower alkoxy, hydroxy, lower alkanoyloxy, aroyloxy, nitro, halogen, trifluoromethyl, lower alkanoyl, aroyl, lower alkylsulfonyl, carbamoyl, N-mono-or N,N-di-lower alkylcarbamoyl, sulfamoyl, N-mono- or N,N-di-lower alkylsulfamoyl; or $R_1'$ and $R_2'$ combined represent together lower alkylidene, benzylidene or diphenylmethylidene; or $R_1'$ and $R_2'$ combined represent together $C_4$-$C_6$ straight chain alkylene; $R_3$ represents hydrogen or lower alkyl; and pharmaceutically acceptable salts thereof.

Particularly preferred are the compounds of formula VI wherein $R_1'$ represents hydrogen; $R_2'$ represents hydrogen, lower alkyl, pyridyl; or $R_2'$ represents benzyl or phenyl each unsubstituted or monosubstituted on phenyl by cyano, lower alkyl, lower alkoxy, hydroxy, lower alkanoyloxy, halogen, nitro, trifluoromethyl, lower alkanoyl, aroyl, lower alkylsulfonyl, carbamoyl, N-mono or N,N-di-lower alkyl-carbamoyl, sulfamoyl, N-mono or N,N-di-lower alkylsulfamoyl; $R_3$ represents hydrogen or lower alkyl; and pharmaceutically acceptable salts thereof.

Preferred in turn are the compounds of formula VI wherein $R_1'$ and $R_3$ represent hydrogen; $R_2'$ represents hydrogen, lower alkyl, benzyl, phenyl, or 3- or 4-pyridyl; or $R_2'$ represents phenyl or benzyl each substituted on phenyl by cyano, halogen, lower alkoxy, lower alkyl or trifluoromethyl; and pharmaceutically acceptable salts thereof.

Most preferred are the compounds of formula VI wherein $R_1'$ and $R_3$ represent hydrogen; $R_2'$ represents 3- or 4-pyridyl, p-cyanobenzyl or p-cyanophenyl; and pharmaceutically acceptable salts thereof.

The general definitions used herein, unless denoted otherwise, have the following meanings within the scope of the present invention.

The term "lower" referred to above and hereinafter in connection with organic radicals or compounds respectively defines such with up to and including 7, preferably up to and including 4 and advantageously one or two carbon atoms.

A lower alkyl group preferably contains 1–4 carbon atoms and represents for example ethyl, propyl, butyl or advantageously methyl.

A lower alkenyl group preferably contains 1–4 carbon atoms and represents for example allyl or crotyl.

A lower alkoxy group preferably contains 1–4 carbon atoms and represents for example methoxy, propoxy, isopropoxy or advantageously ethoxy.

Halogen preferably represents chlorine, but may also be bromine, fluorine or iodine.

Acyl in acyloxy represents lower alkanoyl, aroyl, lower alkoxycarbonyl, or N,N-di-lower alkylcarbamoyl, preferably lower alkanoyl.

Lower alkanoyl is preferably acetyl, propionyl, butyryl, or pivaloyl.

Aroyl is preferably benzoyl or benzoyl substituted by one or two of lower alkyl, lower alkoxy, halogen or trifluoromethyl; aroyl is also thienoyl, pyrroloyl, 2-, 3- or 4-pyridylcarbonyl, advantageously nicotinoyl.

Lower alkanoyloxy is preferably acetoxy, pivaloyloxy or propionyloxy.

Aroyloxy is preferably benzoyloxy or benzoyloxy substituted on the benzene ring by one or two of lower alkyl, lower alkoxy, halogen or trifluoromethyl.

Heteroaroyloxy is preferably 2-, 3- or 4-pyridylcarbonyloxy, advantageously nicotinoyloxy.

Aryl represents a carbocyclic or heterocyclic aromatic radical comprising optionally substituted phenyl, naphthyl, pyridyl, thienyl, indolyl or furyl.

A carbocyclic aromatic radical represents preferably phenyl or phenyl substituted by one or two substituents selected from lower alkyl, lower alkoxy, hydroxy, acyloxy, nitro, amino, halogen, trifluoromethyl, cyano, carboxy, carboxy functionalized in form of a pharmaceutically acceptable ester or amide, lower alkanoyl, aroyl, lower alkylsulfonyl, sulfamoyl, N-lower alkylsulfamoyl and N,N-di-lower alkylsulfamoyl; also 1-or 2- naphthyl, optionally substituted by lower alkyl, lower alkoxy, cyano or halogen.

A heterocyclic aromatic radical represents particularly thienyl, indolyl, pyridyl, furyl or a said heterocyclic radical optionally mono-substituted by lower alkyl, lower alkoxy , cyano or halogen.

Thienyl represents 2- or 3-thienyl, preferably 2-thienyl.

Pyridyl represents 2-, 3- or 4- pyridyl, preferably 3- or 4-pyridyl advantageously 3-pyridyl.

Furyl represents 2-or 3-furyl, preferably 3-furyl.

Indolyl represents preferably 3-indolyl.

Carboxy functionalized in form of a pharmaceutically acceptable ester represents preferably lower alkoxycarbonyl; aryl-lower alkoxycarbonyl, e.g. benzyloxycarbonyl or pyridylmethoxycarbonyl; lower alkanoyloxy-substituted lower alkoxycarbonyl, e.g. pivaloyloxymethoxycarbonyl; or 3-phthalidoxycarbonyl.

Carboxy functionalized in form of a pharmaceutically acceptable amide represents preferably carbamoyl, N-mono-lower alkylcarbamoyl or N,N-di-lower alkylcarbamoyl.

Aryl-lower alkyl represents preferably arylmethyl or arylethyl in which aryl represents a carbocyclic or heterocyclic aromatic radical as defined above, advantageously optionally substituted phenyl as defined above.

Lower alkylidene represents preferably straight chain lower alkylidene, advantageously methylidene or ethylidene.

$C_4$–$C_6$-alkylene represents advantageously butylene or pentylene.

Ortho-phenylene bridged-$C_2$–$C_4$-straight chain alkylene represents $C_2$–$C_4$-straight chain alkylene interrupted by ortho-phenylene, preferably ortho-phenylene bridged $CH_2CH_2$.

$C_3$–$C_6$-cycloalkyl represents preferably cyclopentyl or cyclohexyl.

Pharmaceutically acceptable salts represent acid addition salts with conventional acids, for example mineral acids, e.g. hydrochloric acid, sulfuric or phosphoric acid, or organic acids, for example aliphatic or aromatic carboxylic or sulfonic acids, e.g. acetic, propionic, succinic, glycolic, lactic, malic, tartaric, citric, ascorbic, maleic, fumaric, hydroxymaleic, pyruvic, phenylacetic, benzoic, 4-aminobenzoic, anthranilic, 4-hydroxybenzoic, salicylic, 4-aminosalicylic, pamoic, gluconic, nicotinic, methanesulfonic, ethanesulfonic, halobenzenesulfonic, toluenesulfonic, naphthalenesulfonic, sulfanilic or cyclohexylsulfamic acid; also amino acids, such as arginine and lysine. For compounds of the invention having acidic groups, for example a free carboxy group, pharmaceutically acceptable salts also represent metal or ammonium salts, such as alkali metal or alkaline earth metal salts, e.g. sodium, potassium, magnesium or calcium salts, as well as ammonium salts, which are formed with ammonia or suitable organic amines.

The compounds of the invention which possess an asymmetric carbon atom exist as racemates and the R and S enantiomers thereof. The present invention is intended to include these forms, also diastereoisomers and mixtures thereof if two or more asymmetric centers are present, as well as geometric isomers, e.g. cis and trans isomers if a double bond is present in the molecule.

The compounds of the instant invention have valuable pharmacological properties. For example, they are useful as inhibitors of aromatase activity and inhibitors of estrogen biosynthesis in mammals, and for treating conditions responsive thereto. These compounds inhibit the metabolic conversion of androgens to estrogens in mammals. Thus, the compounds of formula I are useful e.g. in the treatment of gynecomastia, i.e. male breast development, by inhibiting the aromatization of steroids in males susceptible to this condition. Moreover, the compounds of formula I are useful e.g. in the treatment of estrogen dependent diseases in females, for example estrogen dependent female breast cancer, especially in postmenopausal females, by inhibiting estrogen biosynthesis. These effects are demonstrable in in vitro assay tests or in vivo animal tests using advantageously mammals, e.g. guinea pigs, mice, rats, cats, dogs, or monkeys. Additionally, the compounds of formula I are useful e.g. in the prevention of fertility in female mammals; i.e. the prevention of ovulation and implantation. The applied dosage may range between about 0.001 and 30 mg/Kg, preferably between about 0.001 to 5 mg/Kg.

The in vitro inhibition of aromatase activity of the compounds of the present invention can be demonstrated as follows:

A microsomal fraction is prepared from human placenta by the method essentially as described by Thompson and Siiteri, *J. Biol. Chem.*, Vol. 249, p. 5364 (1974). The microsomal preparation so obtained is lyophilized and stored at −40° C.

The assay is conducted substantially as described by Thompson and Siiteri. The human placental microsomes are added to [1,2-$^3$H]-androstenedione and incubated for 20 minutes at 37° C. The amount of aromatization of the labelled substrate is detected by the loss of $^3H_2O$ into the incubation medium. The substrate is removed by chloroform extraction, followed by adsorption to charcoal in suspension. The charcoal is removed by centrifugation and the steroid-free medium is counted in a liquid scintillation counter. Compounds are tested for aromatase inhibitory activity by adding them to the incubation medium prior to the addition of the microsomes. The relative cpm obtained with and without the inhibitor is used to calculate the percent inhibition of the aromatization of androstenedione to estrone. $IC_{50}$ values can be determined graphically as the concentration of test compound at which the aromatization of androstenedione to estrone is reduced to 50% of control value.

The compounds of the invention are effective at concentrations ranging from about $10^{-7}$ M to about $10^{-9}$ M. Illustrative of the invention the compounds of examples 1a, 1c, 2a, 5e and 11f have an $IC_{50}$ of about 10, 1.5, 1.2, 16 and 3 nanomolar, respectively, in the in vitro assay for aromatase inhibition; also the compound of example 20a has an $IC_{50}$ of about 11 nanomolar.

The in vivo inhibition of aromatase activity of the compounds of the present invention can be demonstrated as follows, by measuring the inhibition of estrogen synthesis in rats.

Twenty-one-day-old female rats are injected subcutaneously with 10 IU pregnant mare serum gonadotropin (PMS). Two days later the same rats are injected subcutaneously with 30 IU human chorionic gonadrotropin (hCG). On the day following the hCG treatment the rats are injected subcutaneously with either propylene glycol (0.2 ml; p.o.) or with various doses of the test compound. One hour later all of the rats are treated with 2.25 mg androstenedione in 0.1 ml oil, subcutaneously. Four hours after the injection of androstenedione the rats are sacrificed and their ovaries removed and trimmed free of adhering tissue and stored in pairs at $-40°$ C. To determine the total estrogen content of the ovaries, 1.5 ml of 0.05 M aqueous potassium phosphate buffer, pH 7.4, and 0.2 ml of 0.1 N aqueous sodium hydroxide are added to the tissues which are then homogenized. The homogenate is extracted with 15 ml of diethyl ether, 5 ml aliquots are radioimmunoassayed with antiserum having 100% cross reactivity with estrone, estradiol and estriol. The ovarian estrogen content is expressed as ng estrogen/pair of ovaries. The inhibition of estrogen synthesis, indicative of aromatase inhibition, is calculated from the ovarian estrogen content in treated as compared to control animals.

Illustrative of the invention, the compound of Example 2a inhibit estrogen synthesis at a dose of about 1.5 ug/Kg p.o. in the female rat, and the compounds of examples 5e and 11f inhibit estrogen synthesis at a dose of about 3 ug/Kg p.o.

The antitumor activity, especially in estrogen-dependent tumors, can be demonstrated in vivo e.g. in dimethylbenzanthracene (DMBA)-induced mammary tumors in female Sprague-Dawley rats [see Proc. Soc. Exp. Biol. Med. 160, 296–301 (1979)]. Compounds of the invention cause regression of existing tumors and suppress the appearance of new tumors at daily doses of about 0.01 to about 20 mg/kg p.o. Illustrative of the invention, the compound of Example 2a is effective at a daily dose of about 0.1 mg/Kg p.o administered to rats; the compound of example 20a is effective at a dose of about 0.03 mg/Kg p.o.

The in vivo antifertility property (e.g. inhibition of implantation and/or induction of fetal resorption) of the compounds of the present invention can be demonstrated as follows, by monitoring the implantation and-/or fetal resorption in rats.

Mated female rats (Sprague Dawley) weighing approximately 180–200 g were obtained on the day of coitus. The presence of sperm in the vagina was used as a verification that mating had occurred. On the day of receipt, day of coitus or day 0 of 'pregnancy' the rats are divided into two groups of six to eight rats per group. One group is given various doses of the test compound p.o., suspended in 0.2 ml of carboxymethylcellulose (CMC) beginning on day 1 of 'pregnancy' and continuing through day 9 of 'pregnancy'. These same rats receive a daily injection of 0.1 ml of sesame oil s.c. over this same time frame. The second group of rats receive the vehicles, CMC p.o. and oil s.c., on days 1–9 of 'pregnancy'. All of the rats are sacrificed on day 12 or 13 of 'pregnancy' and their uteri are exposed and examined for fetuses and/or resorption sites.

Illustrative of the invention, the compound of Example 2a administered as the fumarate or hemisuccinate salt inhibits fertility at a dose of about 4 mg/Kg/p.o. in female rats.

Furthermore, the compounds of the invention are essentially devoid of cholesterol side chain cleavage inhibitory activity and do not induce adrenal hypertrophy at effective aromatase inhibitory doses.

Additionally, the compounds of the present invention are useful in delaying proestrus and estrus and further in inhibiting estrus in animals, especially in the dog (canine) and furthermore in the cat (feline).

Pet overpopulation continues to be a serious problem for which human societies have long sought a solution. For example, the attraction of male dogs and possible undesired mating of female dogs during estrus is a serious problem for many responsible pet owners. Surgical ovariohysterectomy is a final procedure with possible long term complications and is not in all cases an acceptable approach, especially where the intent is only to delay estrus in field trial and show dogs or to delay breeding. In later cases, only a postponement of proestrus and estrus or temporary and reversible inhibition of estrus are desired.

Proestrus, for example in the bitch, commences with a vaginal discharge, followed by attraction of the male resulting from estrogen secretion and lasts on an average of 9 days. The females only permit mating during estrus. The compounds of the present invention, when administered to female dogs e.g. on the second day of proestrus, terminate all physical signs of proestrus and estrus and mating will be prevented. Dogs in anestrus which have a known history of previous estrus cycles, mating and conception do not experience estrus during about 224 days of administration of compounds of the present invention.

For example, the cessation of proestrus and estrus, e.g. in the dog can be demonstrated as follows: After initiating oral administration of a compound of the present invention to a female dog, the day after proestrus is detected, the signs of proestrus are eliminated. After 10.0 mg/kg p.o. daily of the compound of example 46 is administered the dogs refused to accept a male dog 9 and 11 days following the initial sign of proestrus. Likewise, when administering a compound of the present invention to a dog in the anestrus phase of the estrous cycle the dogs do not experience estrus. For example, ten mature beagles during anestrus with known breeding histories were administered e.g. 10.0 mg/kg p.o. daily of the compound of example 46 for 224 days. No signs of proestrus were observed in these animals while all control dogs exhibited proestrus and estrus at least once. Ten female beagles with known breeding histories were administered 10.0 mg/kg p.o. daily of the compound of example 46 for 91 days beginning on the first day proestrus was noted. All signs of proestrus disappeared and no dogs accepted a male when presented 9 and 11 days later. Proestrus was not observed during the remainder of the 91 days. During the 190 days recovery period eight of ten dogs exhibited estrus.

Due to their pharmacological properties as selective aromatase inhibitors, the compounds of the invention are useful for the inhibition of estrogen biosynthesis in mammals and the treatment of estrogen dependent disorders responsive thereto, such as mammary tumors (breast carcinoma), endometriosis, premature labor and endometrial tumors in females, as well as gynecomastia in males.

Accordingly, the compounds of the present invention are useful in Relaying proestrus and estrus and in inhibiting of proestrus in the anestrus animal, especially in the canine, and can thus be used as birth control agents in the animal, especially in the canine.

As a consequence of the antifertility property of the compounds of the present invention, these compounds may find use not only in the antifertility uses generally thought of but may also find use in reducing rodent and other mammalian pest populations wherein the reproductive cycle is estrogen dependent.

The compounds of formula I or II–VI may be prepared as follows:

a) for compounds of formula I wherein W represents 1-imidazolyl or 1-triazolyl each optionally substituted by lower alkyl, condensing a compound of the formula VII $$W'-H \qquad (VII)$$

wherein W' represents 1-imidazolyl or 1-triazolyl each optionally substituted by lower alkyl, or an N-protected derivative thereof particularly where W represents 1-imidazolyl or lower alkyl-substituted-1-imidazolyl, with a reactive esterified derivative of a compound of the formula VIII

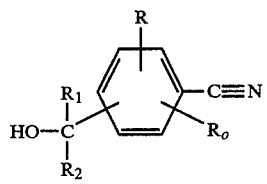

(VIII)

wherein R, R$_o$, R$_1$ and R$_2$ have meaning as defined herein for formula I;

b) for compounds wherein W represents 3-pyridyl optionally substituted by lower alkyl, dehalogenating a compound of the formula IX

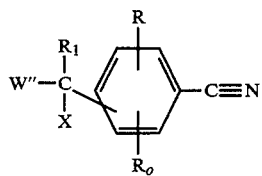

(IX)

wherein W'' represents 3-pyridyl optionally substituted by lower alkyl, X represents halogen, preferably chloro, R and R$_o$ have meaning as defined herein for compounds of formula I and R$_1$ has meaning as defined herein for formula I; and if required reacting the resulting product of formula X

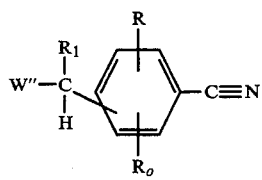

(X)

with a reactive derivative of the radical R$_2$ using process c) below;

c) condensing under basic conditions a compound of the formula XI

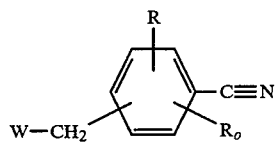

(XI)

(being a compound of formula I wherein R$_1$ and R$_2$ represent hydrogen) wherein R, R$_o$ and W have meaning as defined herein for formula I, with a reactive functional derivative of a radical R$_1$ or R$_2$ (R$_1$ or R$_2$ not representing hydrogen), so as to obtain a compound of formula I wherein only one of R$_1$ and R$_2$ represents hydrogen; or similarly condensing a compound of formula I so obtained with a reactive functional derivative of a radical R$_1$ or R$_2$ (R$_1$ or R$_2$ not representing hydrogen) to obtain a compound of formula I wherein neither R$_1$ nor R$_2$ represents hydrogen; or condensing a compound of the formula XI with a reactive bifunctional derivative of R$_1$ and R$_2$ combined representing C$_4$–C$_6$ straight alkylene, lower alkyl substituted C$_4$–C$_6$ straight chain alkylene or 1,2-phenylene-bridged-C$_2$–C$_4$ straight chain alkylene to obtain a corresponding compound of formula I;

d) converting R$_5$ to cyano in a compound of the formula XII

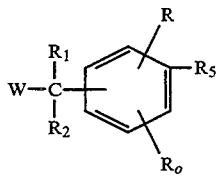

(XII)

wherein W, R, R$_o$, R$_1$ and R$_2$ have meaning as defined above and R$_5$ represents a group or radical that can be converted to the cyano group;

e) converting a compound of formula I into another compound of formula I; and/or converting a free compound into a salt, and/or converting a salt into a free compound or into another salt; and/or separating a mixture of isomers or racemates into the single isomers or racemates and/or resolving a racemate into the optical isomers.

In starting compounds and intermediates which are converted to the compounds of the invention in a manner described herein, functional groups present, such as carboxy, amino (including ring NH) and hydroxy groups, are optionally protected by conventional protecting groups that are common in preparative organic chemistry, Protected carboxy, amino and hydroxy groups are those that can be converted under mild conditions into free carboxy, amino and hydroxy groups without the molecular framework being destroyed or other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (carboxy group, amino group, etc.), the structure and stability of the molecule of which the substituent is a part, and the reaction conditions.

Well-known protecting groups that meet these conditions and their introduction and removal are described, for example, in J. F. W. McOmie, "Protective Groups in Organic Chemistry", Plenum Press, London, New York, 1973, T. W. Greene, "Protective Groups in Organic Synthesis", Wiley, New York, 1984, Relating to the above processes, a reactive functional derivative of the radicals $R_1$ and $R_2$ represents said radicals substituted by a leaving group, preferably by lower alkyl-or aryl-sulfonyloxy, e.g. mesyloxy or toluenesulfonlyloxy, or by halogen, e.g. fluoro, chloro, bromo or iodo. Similarly, a reactive esterifed derivative of an alcohol, e.g. of a compound of formula VIII represents said alcohol esterified in the form of a leaving group, e.g. lower alkyl- or aryl-sulfonyloxy, such as mesyloxy or toluenesulfonyloxy, or halogen, such as chloro, bromo or iodo.

Protecting groups for the imidazolyl nitrogen are preferably tri-lower alkylsilyl, e.g. trimethylsilyl, lower alkanoyl, e.g. acetyl, di-lower alkylcarbamoyl such as dimethylcarbamoyl, or triarylmethyl, e.g. triphenylmethyl.

The condensation according to process (a) is carried out according to N-alkylation procedures well-known in the art, either as such or in the presence of a base such as triethylamine or pyridine in an inert solvent, e.g. dichloromethane, at room temperature or near the boiling of the solvent used.

In the case of protected imidazolyl, alkylation occurs on the second unprotected nitrogen to first form a quaternary compound which is advantageously simultaneously deprotected in situ prior to the isolation of the product. The imidazole and triazole starting materials of formula VII are either known or are prepared according to methods known in the art.

The nitrile substituted starting materials representing reactive esterified derivatives of the carbinols of formula VIII are also either known or are prepared e.g. as illustrated below and the examples herein. For example, the halo substituted starting materials can be advantageoulsy prepared using the following illustrative sequence of reactions using appropriate reaction conditions known in the art and illustrated in the examples.

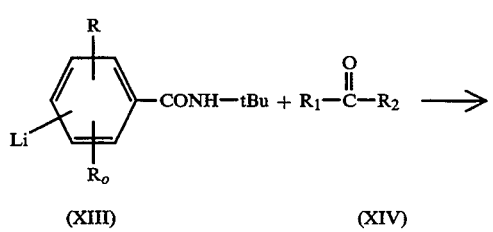

(XIII)      (XIV)

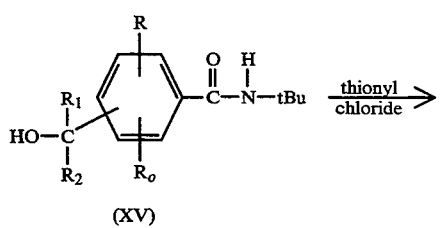

(XV)

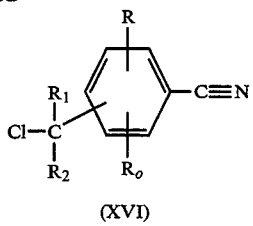

(XVI)

The starting materials of formula XIV represent appropriate aldehydes or ketones in which $R_1$ and $R_2$ correspond to relevant definitions in formula I.

For compounds of formula I wherein $R_1$ represents hydrogen and $R_2$ represents cyanophenyl, the intermediate corresponding to formula XV can be advantageously prepared by reacting the lithium organometallic reagent of formula XIII with ethyl formate (instead of compound of formula XIV) in the above sequence of reactions.

It should also be noted that in the above intermediate XIII, the CONH-t-Bu substituent may be replaced by cyano or any other grouping suitable for the condensation and known in the art to be convertible into cyano. Such groupings are included under process (d) ($R_5$ in formula XII).

The dehalogenation under process (b) for the preparation of the compounds of formula I wherein W represents pyridyl optionally substituted by lower alkyl can be achieved advantageously with zinc in acetic acid. Other suitable reagents include tributyl tin hydride or aluminum amalgam.

The starting halides of formula IX can be prepared from an alcohol with a halogenating agent, e.g. thionyl chloride as described under process a). The alcohol can in turn be prepared by condensation of a compound of formula XIII or the like with an appropriate aldehyde or ketone of the formula XVII

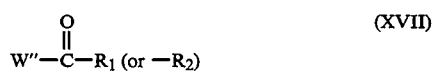

in which $R_1$ and $R_2$ correspond to relevant definitions for $R_1$ and $R_2$ in formula I and W'" represents 3-pyridyl.

The condensation according to process (c) is carried out according to procedures generally known in the art for displacement e.g. of a halo, lower alkyl- or arylsulfonyloxy leaving group.

The condensation is carried out in a conventional manner by first forming a carbanion in the presence of a strong base such as lithium diisopropylamide, an alkali metal hydride, an alkali metal alkoxide such as potassium t-butoxide, or a strongly basic tertiary amine such as 1,5-diazabicyclo[4.3.0]non-5-ene(DBN), preferably in an inert atmosphere, for example under nitrogen atmosphere and in a polar solvent such as dimethylformamide.

For compounds of formula I wherein $R_1$ and/or $R_2$ represents p-cyanophenyl a suitable reactive derivative is p-fluorobenzonitrile. For compounds wherein $R_1$ or $R_2$ represents (lower alkyl, aryl or aryl-lower alkyl)-thio, suitable reactive derivatives are the disulfides corresponding thereto, such as diphenyl disulfide or dimethyl disulfide.

Process (d) is carried out according to known methods for the introduction of a nitrile group.

A group or radical $R_5$ in a compound of formula XII which can be converted into the CN group, is, for example, hydrogen, esterified hydroxy, for example halo, especially chloro, bromo, or iodo, or a sulfonyloxy group, for example p-toluenesulfonyloxy, benzenesulfonyloxy or mesyloxy, sulfo, amino, carboxy, carboxy in the form of a functional derivative, for example carbamoyl, lower alkylcarbamoyl, for example t-butyl-carbamoyl, or haloformyl, for example chloro- or bromoformyl, formyl, a formyl group in the form of a functional derivative, for example hydroxyiminomethyl, or a halomagnesium group, for example iodo-, bromo- or chloromagnesium.

Compounds of the formula I ( or II–VI ) can be obtained, for example, by carrying out the following convetsions:

The conversion of a compound of the formula XII wherein $R_5$ is hydrogen, to the corresponding nitrile of the formula I is performed e.g. according to the known method of C. Friedel, F. M. Crafts and P. Karrer by reacting with cyanogen chloride (ClCN) or cyanogen bromide or according to the method of J. Houben and W. Fisher, by reacting with e.g. trichloroacetonitrile. Advantageously, the standard catalyst aluminum chloride is used in these reactions and hydrogen chloride or hydrogen bromide is released which can be removed from the reaction mixture after addition of a base, preferably an amine, for example triethylamine or pyridine.

The conversion of a compound of the formula XII wherein $R_5$ is halo, for example, chloro, bromo or iodo, to a corresponding nitrile of the formula I is performed by using e.g. a cyanide salt, especially sodium or potassium cyanide or, preferably, copper(I) cyanide. Preferred solvents for this reaction are pyridine, quinoline, dimethylformamide, 1-methyl-2-pyrrolidinone and hexamethylphosphoric triamide. High temperatures, especially reflux temperatures of the reaction mixture are preferred.

The conversion of a compound of the formula XII wherein $R_5$ is a sulfonyloxy group, for example p-toluenesulfonyloxy, benzenesulfonyloxy or mesyloxy, to a nitrile of the formula I is performed e.g. by reaction with an alkali metal cyanide, preferably sodium or potassium cyanide. High temperatures, especially the reflux temperature of the reaction mixture, are preferred.

The conversion of a compound of the formula XII wherein $R_5$ is amino, to a nitrile of the formula I proceeds over several steps. First, a diazonium salt is formed e.g. by reaction of the amino compound with an alkali metal nitrite preferably potassium nitrite. The diazonium salt can be reacted using the well-known Sandmeyer reaction in situ e.g. with cuprous cyanide or a cyanide complex preferably potassium cuproammonium cyanide, or with catalytic amounts of freshly precipitated copper powder in the presence of an alkali metal cyanide, for example sodium or potassium cyanide.

The conversion of a compound of formula XII wherein $R_5$ is carboxy to a nitrile of formula I can be carried out by reaction with chlorosulfonylisocyanate in e.g. dimethylformamide according to the method of R. Graf, Angew. Chem. 80, 183 ( 1968 ).

The conversion of a compound of the formula XII wherein $R_5$ is a carboxy group in the form of a functional derivative, for example carbamoyl, lower alkylcarbamoyl, advantageously t-butylcarbamoyl, to a nitrile of the formula I can be carried out e.g. with a strong dehydrating agent, such as phosphorus pentoxide, phosphoryl chloride, thionyl chloride, phosgene or oxalyl chloride. The dehydration can be preferably carried out in the presence of a suitable base. A suitable base is, for example, an amine, for example a tertiary amine, for example tri-lower alkylamine, for example trimethylamine, triethylamine or ethyl diisopropylamine, or N,N-di-lower alkylaniline, for example N,N-dimethylaniline, or a cyclic tertiary amine, for example a N-lower alkylated morpholine, for example N-methylmorpholine, or is, for example, a base of the pyridine type, for example pyridine or quinoline.

The conversion of a compound of formula XII wherein $R_5$ is formyl to a nitrile of formula I is carried out e.g. by converting the formyl group to a reactive functional derivative, for example a hydroxyiminomethyl group, and converting this group to cyano by a dehydrating agent. A suitable dehydrating agent is one of the inorganic dehydrating agents mentioned above, for example phosphorous pentachloride, or, preferably, the anhydride of an organic acid, for example the anhydride of a lower alkane carboxylic acid, for example acetic acid anhydride. The conversion of the formyl group to hydroxyiminomethyl is carried out by reacting a compound of formula IX wherein $R_5$ is formyl, e.g. with an acid addition salt of hydroxylamine, preferably the hydrochloride.

A compound of the formula XII wherein $R_5$ is formyl can also be converted directly to a corresponding nitrile of the formula I e.g. by reaction with O,N-bis-(trifluoroacetyl)-hydroxylamine in the presence of a base, for example pyridine, according to the method of D. T. Mowry, Chem. Rev. 42, 251 (1948).

The conversion of a compound of the formula XII wherein $R_5$ is a halomagnesium group, for example, iodo-, bromo-, or chloromagnesium, to a corresponding nitrile of the formula I is performed e.g. by reacting the magnesium halide with cyanogen halide or dicyanogen. The "Grignard" reagent, wherein $R_5$ is a halomagnesium group, is prepared in a conventional manner, for example by reacting a compound of the formula XII wherein $R_5$ is halo, for example chloro, bromo or iodo, with magnesium, e.g. in dry ether.

The compounds of the invention obtained by the above-cited processes can be converted into other compounds of the invention of formula I according to methodology known in the art and as illustrated herein.

Compounds of formula I, substituted by e.g. an acyloxy group, such as lower alkanoyloxy or aroyloxy, may be converted to compounds of formula I substituted by hydroxy, by hydrolysis with e,g. aqueous acid such as hydrochloric acid, or with aqueous alkali, such as lithium or sodium hydroxide.

Conversely, the conversion of compounds of formula I substituted by hydroxy to compounds of formula I substituted by acyloxy, such as alkanoyloxy or aroyloxy, may be carried out by condensation with a corresponding carboxylic acid, or a reactive functional derivative thereof, according to alkylation (esterification) procedures well-known to the art.

The conversion of the compounds of formula I substituted by an etherified hydroxy group, e.g. lower alkoxy, to the compounds of formula I substituted by a hydroxy group is carried out by methods well-known in the art, e.g., with a mineral acid, such as hydriodic acid or, advantageously for compounds wherein lower alkoxy is methoxy, with e.g. boron tribromide in methylene chloride or with sodium or lithium diphenylphosphine in tetrahydrofuran.

The compounds of formula I wherein $R_1$ and $R_2$ represent hydrogen, i.e. the compounds of formula XI, may be converted to the compounds of formula I wherein $R_1$ and $R_2$ combined represent lower alkylidene, mono- or diaryl-lower alkylidene by reacting said compounds of formula XI with an appropriate aldehyde or ketone in the presence of a strong base, e.g. lithium diisopropylamide, and, if required, treating the resulting alcohols with a dehydrating agent, such as thionyl chloride.

Furthermore, the compounds of formula I wherein at least one of $R_1$ and $R_2$ represents hydrogen are converted to other compounds of formula I as described above under process c ).

Unless stated otherwise, the above reactions are preferably carried out in an inert, preferably anhydrous, solvent or solvent mixture, for example in a carboxylic acid amide, for example a formamide, for example dimethylformamide, a halogenated hydrocarbon, for example methylene chloride or chloroform, a ketone, for example acetone, a cyclic ether, for example tetrahydrofuran, an ester, for example ethyl acetate, or a nitrile, for example acetonitrile, or in mixtures thereof, optionally at reduced or elevated temperature, for example in a temperature range from approximately $-50°$ C. to approximately $+150°$ C. preferably from room temperature to the boiling temperature of the reaction mixture and optionally under inert gas atmosphere, for example nitrogen atmosphere, and at atmospheric pressure.

The invention further includes any variant of the present processes, in which an intermediate product obtainable at any stage thereof is used as starting material and the remaining steps are carried out, or the process is discontinued at any stage thereof, or in which the starting materials are formed under the reaction conditions or, in which the reaction components are used in the form of their salts or optically pure antipodes, Whenever desirable, the above processes are carried out after first suitably protecting any potentially interfering reactive functional groups, as illustrated above and in the examples herein.

Advantageously, those starting materials should be used in said reactions, that lead to the formation of those compounds indicated above as being preferred, The invention also relates to novel starting materials and processes for their manufacture.

Depending on the choice of starting materials and methods, the new compounds may be in the form of one of the possible isomers or mixtures thereof, for example, as pure geometric isomers (cis or trans), as pure optical isomers (as antipodes), or as mixtures of optical isomers such as racemates, or as mixtures of geometric isomers.

In case geometric or diastereomeric mixtures of the above compounds of intermediates are obtained, these can be separated into the single racemic or optically active isomers by methods in themselves known, e.g. by fractional distillation, crystallization and/or chromatography.

The racemic products or basic intermediates can be resolved into the optical antipodes, for example, by separation of diastereomeric salts thereof, e.g., by the fractional crystallization of d- or l-(tartrate, dibenzoyltartrate, mandelate or camphorsulfonate) salts.

Any acidic intermediates or products can be resolved by separation of e.g. the d- and l-(alpha-methylbenzylamine, cinchonidine, cinchonine, quinine, ephedrine, dehydroabietylamine, brucine or strychnine)-salts of any compounds having an acidic salt-forming group.

Advantageously, the more active of the antipodes of the compounds of this invention is isolated.

Finally, the compounds of the invention are either obtained in the free form, or as a salt thereof. Any resulting base can be converted into a corresponding acid addition salt, preferably with the use of a pharmaceutically acceptable acid or anion exchange preparation, or resulting salt can be converted into the corresponding free bases, for example, with the use of a stronger base, such as a metal or ammonium hydroxide, or any basic salt, e.g., an alkali metal hydroxide or carbonate, or a cation exchange preparation, These or other salts, for example, the picrates, can also be used for purification of the bases obtained; the bases are converted into salts, In view of the close relationship between the free compounds and the compounds in the form of their salts, whenever a compound is referred to in this context, a corresponding salt is also intended, provided such is possible or appropriate under the circumstances.

The compounds, including their salts, may also be obtained in the form of their hydrates, or include other solvents used for the crystallization.

The present invention further relates to the use in mammals of the compounds of formula I and II–VI and their pharmaceutically acceptable acid addition salts, or pharmaceutical compositions thereof, as medicaments, particularly as aromatase inhibitors and as inhibitors of estrogen biosynthesis, particularly for the treatment and amelioration of estrogen dependent conditions, such as gynecomastia, mammary tumors, endometrial tumors, endometriosis and premature labor.

A particular embodiment of the invention thus relates to a method of inhibiting aromarase activity and thereby suppressing estrogen synthesis in mammals by administering an effective aromatase inhibiting amount of a compound of the invention, e.g. of formula I, or II, III, IV, V or VI or a pharmaceutically acceptable salt thereof, or of a pharmaceutical composition comprising said compound, to a mammal in need thereof.

The present invention is thus also particularly directed to the method of treatment in mammals of conditions responsive to aromatase inhibition, particularly estrogen dependent diseases, e.g. estrogen dependent tumors such as mammary tumors, by administering an effective aromatase inhibiting and estrogen biosynthesis inhibiting amount of a compound of the invention or of a pharmaceutical composition comprising such compound, to a mammal in need thereof.

The present invention is further directed to a method of inhibiting fertility in female mammals (e.g. by inhibiting ovulation, inhibiting implantation, inducing fetal resorption) which comprises administering an effective amount of a compound of the invention or of a pharmaceutical composition comprising such compound.

The present invention is further directed to a method of delaying proestrus and estrus and in inhibiting proestrus in the anestrus animal, especially in the canine, and can thus be used as birth control agents in the female animal in need thereof, especially in the canine, by administering to a female animal an effective amount of a compound of the present invention or a veterinarily acceptable salt thereof; or of a veterinary composition comprising said compound in combination with one or more veterinarily acceptable carriers.

The dosage of active compound administered is dependent on the species of warm-blooded animal (mammal), the body weight, age and individual condition, and on the form of administration.

A unit dosage for a mammal of about 50 to 70 kg may contain between about 0.05 and 25 mg of an active ingredient.

The present invention also relates to the use of the compounds of the invention for the preparation of pharmaceutical compositions, especially pharmaceutical compositions having aromatase inhibiting or estrogen biosynthesis inhibiting properties.

The pharmaceutical compositions according to the invention are those suitable for enteral, such as oral or rectal, transdermal and parenteral administration to mammals, including man, for the treatment of estrogen-dependent diseases responsive to aromatase inhibition, comprising an effective aromatase inhibiting amount of a pharmacologically active compound of formula I, or II, III, IV, V or VI or a pharmacologically acceptable salt thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the Active ingredient together with a) diluents, e.g. lactose, dextrose, sucrose, mannitol, sorbitol, cellulose and/or glycine; b) lubricants, e.g. silica, talcum, stearic acid, its magnesium or calcium salts and/or polyethyleneglycol; for tablets also c) binders, e.g. magnesium aluminum silicate, starch paste, gelatin, tragacanth, methylcellulose, sodium carboxymethylcellulose and/or polyvinylpyrrolidone; if desired, d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain preferably about 1 to 50% of the active ingredient.

Suitable formulations for transdermal application include an effective amount of a compound of formula I, or II–VI with carrier. Advantageous carriers include absorbable pharmaceutically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. The structure of final products, intermediates and starting materials is confirmed by analytical methods, e.g. microanalysis and spectroscopic characteristics (e.g. MS, IR, NMR).

EXAMPLE 1 a) A solution of alpha-bromo-4-tolunitrile (86.6 g) in dichloromethane ( 1000 mL) is mixed with imidazole ( 68.0 g). The mixture is stirred at ambient temperature for 15 hours and then diluted with water (1000 mL). Any undissolved solid is removed by filtration and the separated organic solution is then repeatedly washed with water ($5 \times 200$ mL) to remove excess imidazole, and then dried (MgSO$_4$). The crude product obtained upon evaporation of the solvent can be purified by trituration with cold diethyl ether (200 mL) to obtain 4-( 1-imidazolylmethyl)-benzonitrile, m.p. 99–101°; HCl salt, m.p. 142°–144.

Similarly prepared are:

b) 2-(1-imidazolylmethyl)-benzonitrile hydrochloride, m.p. 176°–177;

c) 4-(1-imidazolylmethyl)-l-naphthonitrile hydrochloride, m.p. 210°–212° dec.;

EXAMPLE 2 a) A suspension of potassium tert-butoxide (61.6 g) in dimethylformamide (500 mL) is stirred and cooled to $-10°$ (ice-salt bath), and a solution of 4-(1-imidazolylmethyl)-benzonitrile (45.6 g) in dimethylformamide (250 mL) is added so that the reaction temperature remains below 0°. The resulting solution is stirred at 0° for 0.5 hour and then a solution of 4-fluorobenzonitrile ( 38.3 g ) in dimethylformamide ( 100 mL) is added while keeping reaction temperature below 5°. After 0.75 hour, the reaction mixture is neutralized to pH 7 by addition of sufficient 3 N hydrochloric acid and the bulk of the solvents are then removed under reduced pressure. The residue is diluted with water (500 mL) and the crude product is extracted into ethyl acetate ($3 \times 200$ mL). The combined extracts are then extracted with 3 N hydrochloric acid ($3 \times 150$ mL) and, after washing the latter acid extracts with ethyl acetate (100 mL), the solution is made basic (pH 8) with 6 N ammonium hydroxide and the product is again extracted into ethyl acetate ($3 \times 150$ mL). The combined extracts are dried (MgSO$_4$), decolorized by treatment with charcoal, and then evaporated to give crude 4-[alpha-(4-cyanophenyl)-1-imidazolylmethyl]-benzonitrile as an oil. This material is dissolved in isopropanol (250 mL) and the warm solution is stirred with succinic acid (14.4 g). Upon dilution with diethyl ether (100 mL) and stirring at ambient temperature, the hemi-succinate salt separates. The salt is filtered off, washed with a little cold isopropanol and then air dried to afford 4-[alpha-(4-cyanophenyl)-1-imidazolylmethyl]-benzonitrile hemisuccinate, m.p. 149°–150°. The hemifumarate salt has m.p. 157°–158°.

Similarly prepared are:

b ) 4-[alpha-(2-cyanophenyl)-1-imidazolylmethyl]-benzonitrile, IR(CN) 2240 cm$^{-1}$, M/e 384; HCl salt (hygroscopic), m.p. 90° ( dec );

c ) 4- 8 alpha-(4-trifluoromethylphenyl)-1-imidazolylmethyl]-benzonitrile, IR(CN) 2232 cm$^{-1}$, M/e 327; HCl salt (hygroscopic), m.p. 100° (dec).

EXAMPLE 3 a) A solution of 4-(alpha-chloro-4'-cyanobenzyl)benzonitrile (20.2 g) and imidazole (16.3 g) in dimethylformamide (130 mL) is stirred and heated at 160° for 2 hours. The reaction is cooled, diluted with water (800 mL) and extracted into ethyl acetate ($3 \times 150$ mL). The remainder of the work-up is carried out in the manner described in Example 2 to yield 4-[alpha-(4-cyanophenyl)-1-imidazolylmethyl]-benzonitrile hemisuccinate, m.p. 148°-150°.

The starting material, 4-(alpha-chloro-4'-cyanobenzyl)-benzonitrile is prepared as follows:

A solution of N-tert-butyl-4-bromobenzamide (37.2 g) in anhydrous tetrahydrofuran (1000 mL) is stirred under an atmosphere of $N_2$ and cooled to −60°. A solution of n-butyl lithium (125 mL, 2.4 M in hexane, 0.300 mole) is then added during 40 rain and the resulting suspension is stirred for a further 40 min at −60°. A solution of ethyl formate (5.3 g) in anhydrous tetrahydrofuran (50 mL) is then added dropwise during 10 rain and the reaction is allowed to proceed at −60° for 2 hours. The reaction is then quenched by the addition of saturated aqueous ammonium chloride (200 mL) and after allowing the mixture to reach room temperature, diethyl ether (300 mL) is added and the layers are separated. The ethereal solution is washed with water (2×100 mL) and brine (100 mL) and dried (MgSO$_4$). The solvent is evaporated and the residue is triturated with diethyl ether (150 mL) to afford the bis( 4-N-tert-butylcarbamoylphenyl )methanol, m.p. 200°-202°.

Bis-(4-N-tert-butylcarbamoylphenyl )methanol (17.6 g) is suspended in thionyl chloride (140 mL) and the mixture is stirred at reflux for 6 hours. The solvent is evaporated and the residue is taken up in toluene (100 mL) and the solvent is evaporated. The latter procedure is repeated once more to afford the 4-(alpha-chloro-4'-cyanobenzyl)benzonitrile as an oil which is used directly; NMR(CH methine) 3.85 ppm.

EXAMPLE 4

Imidazole (9.4 g) and 4-( alpha-chloro-4'-cyanobenzyl)-benzonitrile (11.6 g) are intimately mixed and heated together in an oil bath at 110°-120° for 15 hours. The reaction mixture is diluted with water (200 mL) and extracted with ethyl acetate (3×75 mL). The remainder of the work-up is carried out as described in Example 2, yielding 4-[alpha-(4-cyanophenyl )-1-imidazolylmethyl]-benzonitrile. The crude product is treated with an equivalent amount of fumaric acid in warm isopropanol to yield 4-[alpha-(4-cyanophenyl)1-imidazolylmethyl]-benzonitrile hemifumarate, m.p. 156°-157°.

EXAMPLE 5

The following compounds are prepared according to the methods described in previous examples 3 and 4 using the appropriate starting materials.

a ) 2-[alpha-(4-bromophenyl)-1-imidazolylmethyl]-benzonitrile, M/e 337;

b) 4-[alpha-4-chlorophenyl)-1-imidazolylmethyl]-benzonitrile; M/e=293; hydrochloride salt, m.p. 90° dec.

c) 4-[alpha-(4-methoxyphenyl)-1-imidazolylmethyl]-benzonitrile, IR(CN) 2235 cm$^{-1}$ M/e 289; hydrochloride salt(hygroscopic), m.p. 90° (dec); d) 4-[alpha-(2-methoxyphenyl)-1-imidazolylmethyl]-benzonitrile, IR(CN) 2234 cm$^{-1}$ M/e 289; hydrochloride salt(hygroscopic), m.p. 95° (dec);

e) 4-[alpha-(3-pyridyl )-1-imidazolylmethyl]-benzonitrile, IR(CN) 2237 cm$^{-1}$ M/e 260; dihydrochloride salt(hygroscopic), m.p. 150°; sulfate salt, m.p. 238°-240°.

f) 4-[alpha-(2-thienyl )-1-imidazolylmethyl]-benzonitrile, IR(CN) 2237 cm$^{-1}$; M/e 265; hydrochloride salt, m.p. 65° dec.

g) 4-[alpha-(3-thienyl )-1-imidazolylmethyl]-benzonitrile, IR(CN) 2240 cm$^{-1}$ M/e 265; hydrochloride salt, m.p. 70° dec.

h) 4-(alpha-phenyl-1-imidazolylmethyl)-benzonitrile; M/e 259; hydrochloride salt, m.p. 90° dec. (hygroscopic);

i) 4- 8 alpha-(4-tolyl )-1-imidazolylmethyl]-benzonitrile; M/e 273; hydrochloride salt, m.p. 90° (dec), hygroscopic;

j) 3-(alpha-phenyl-1-imidazolylmethyl)-benzonitrile; M/e 259; hydrochloride salt(hygroscopic), m.p. 80° (dec);

The starting precursor for compound b is prepared as follows:

A solution of n-butyl lithium (20 mL of 2.4 M reagent, 0.048 mole) in hexane is added dropwise under an atmosphere of $N_2$ to a solution of N-tert-butyl-4-bromobenzamide ( 6.1 g, 0. 024 mole ) in tetrahydrofuran ( 100 mL) which is maintained at −60° and then a solution of 4-chlorobenzaldehyde ( 5.1 g, 0. 036 mole ) in tetrahydrofuran (50 mL) is added dropwise. The reaction is stirred for 2 h at −60° and then quenched by the addition of saturated aqueous ammonium chloride (30 mL) and ether (100 mL). The ethereal layer is separated and washed repeatedly (3×30 mL) with aqueous sodium bisulfite and finally with brine and dried (MgSO$_4$). Solvent evaporation affords (4-chlorophenyl )-(4'-N-tert-butylcarbamoylphenyl)methanol as an oil, NMR(CH methine): 4.30 ppm, which can be used without further purification.

The following carbinols are prepared in a similar manner using an appropriate starting material: phenyl-(4'-N-tert-butylcarbamoylphenyl )methanol, NMR (CH roethine) 4,27 ppm; (4-methoxyphenyl )-(4'-N-tert-butylcarbamoylphenyl) methanol, NMR(CH methine) 4.23 ppm; (2-methoxyphenyl)-(4'-N-tert-butylcarbamoylphenyl) methanol, NMR(CH methine) 4.00 ppm; (4-methylphenyl)-(4'-N-tert-butylcarbamoylphenyl) methanol, NMR(CH methine) 4.23 ppm; (3-pyridyl)-(4'-N-tert-butylcarbamoylphenyl)methanol, NMR(CH methine) 4.20 ppm; (2-thienyl)-(4'-N-tert-butylcarbamoylphenyl)methanol, NMR(CH methine) 3.98 ppm; (3-thienyl)-(4'-N-tert-butylcarbamoylphenyl)methanol, NMR(CH methine) 4.05 ppm; 3-(alpha-hydroxybenzyl)-benzonitrile, NMR(CH methine) 4.20 ppm.

The appropriate starting cyanophenyl substituted chlorides corresponding to the above carbinols are prepared by treatment with thionyl chloride as previously described in Example 3.

EXAMPLE 6

A solution of 4-[alpha-(4-cyanophenyl) -1-imidazolylmethyl]benzonitrile (5.3 g) in dimethylformamide (20 mL) is added dropwise to a cooled (ice-bath) stirred suspension of potassium tert-butoxide (2.5 g) in dimethylformamide (20 mL). This mixture is stirred for 30 rain at 0°-5° and then a solution of methyl iodide (3.5 g) in dimethylformamide (10 mL) is added during 10 min. After stirring at 0°-5° for a further 15 rain, the reaction is diluted with water (200 mL) and extracted with ethyl acetate (3×60 mL). The organic solution is washed with water (50 mL) and then extracted with 3 N hydrochloric acid (3×30 mL). The extracts are made basic (pH 8) with aqueous sodium hydroxide and the product is again extracted into ethyl acetate (2×50 mL). The extracts are dried (MgSO$_4$) and evaporated to give a solid which is recrystallized from isopropanol to give 4-[alpha-(4-cyanophenyl)-alpha-methyl-1-imidazolyl-methyl]benzonitrile, m.p. 184°–186°.

EXAMPLE 7 a) A solution of boron tribromide (11.7 g) in dichloromethane (50 mL) is added dropwise during 30 rain to a cooled (ice-bath) stirred solution of 4-[alpha-(4-methoxyphenyl)-1-imidazolylmethyl]benzonitrile (3.2 g) in dichloromethane (50 mL). The reaction is allowed to proceed at ambient temperature for 15 hours and is then poured onto ice and water (100 mL). The pH is adjusted to 7 by the addition of solid sodium bicarbonate and the layers are separated. The organic solution is washed with water, dried (MgSO$_4$) and evaporated. The residual crude product is triturated with diethyl ether to give 4-[alpha-(4-hydroxyphenyl)-1-imidazolylmethyl]benzonitrile, m.p. 196°–198°.

b) 4-[alpha-(2-hydroxyphenyl)-1-imidazolylmethyl]-benzonitrile, m.p. 230°–235° dec. is similarly prepared.

c) 4-[alpha-(4-hydroxybenzyl)-1-imidazolylmethyl]-benzonitrile, m.p. 238°–240° is also similarly prepared.

EXAMPLE 8

A solution containing 2-[alpha-(4-bromophenyl)-1-imidazolylmethyl]benzonitrile (2.1 g) and hydrazine hydrate (10 mL) in 95% ethanol (60 mL) is mixed with 10% Pd-C catalyst (0.5 g) and the mixture is stirred at reflux for 2½ hours. The catalyst is filtered off and the solvent evaporated to give an oil which is dissolved in 3 N hydrochloric acid (20 mL). The acid solution is extracted with ethyl acetate (10 mL), neutralized to pH 7 with aqueous sodium hydroxide and extracted with ethyl acetate (3×10 mL). The extracts are dried (MgSO$_4$) and evaporated to give the crude product which is further purified by flash column chromatography on silica gel. Elution with ethyl acetate affords 2-[alpha-phenyl-1-imidazolylmethyl]benzonitrile; IR(CN): 2240 cm$^{-1}$; M/e 259; hydrochloride salt, melting with dec.

EXAMPLE 9

A solution containing alpha-bromo-4-tolunitrile (19.6 g) and 1,2,4-triazole (30.5 g) in a mixture of chloroform (250 mL) and acetonitrile (50 mL) is stirred at reflux for 15 hours. The solution is cooled and washed with 3% aqueous sodium bicarbonate (200 mL) and the organic solution is then dried (MgSO$_4$) and evaporated. The residue is chromatographed on silica gel (300 g). Elution with chloroform/isopropanol (10:1) affords 4-[1-(1,2,4-triazolyl)methyl]-benzonitrile, m.p.77°–79° which forms a hydrochloride salt, m.p. 200°–205° when its solution in ethyl acetate is treated with ethereal HCl.

Further elution of the silica gel column with chloroform/isopropanol (3:2) affords 4-[1-(1,3,4-triazolyl)methyl]-benzonitrile, m.p.151°–153°, which forms a hydrochloride salt, m.p. 236°–238°.

EXAMPLE 10

A solution containing alpha-bromo-4-tolunitrile (11.0 g), 1-(dimethylcarbamoyl)-4-methylimidazole (8.6 g) and sodium iodide (8.4 g) in acetonitrile (75 mL) is heated and stirred at reflux for 15 hours. The mixture is cooled to 0° (ice-bath) and ammonia gas is bubbled through the solution for 15 minutes. The volatiles are then evaporated and the residue is partitioned between water (150 mL) and ethyl acetate (150 mL). The organic solution is washed with water (2×50 mL) and is then extracted with 3 N hydrochloric acid. The combined acidic extracts are made basic (pH 9) with 6 N sodium hydroxide and the product is extracted into ethyl acetate (3×60 mL). After drying (MgSO$_4$), solvent evaporation affords crude 4-[1-(5-methylimidazolyl)methyl]-benzonitrile which forms a hydrochloride salt, m.p 203°–205°, when its solution in acetone is treated with ethereal HCl.

The starting material is prepared in the following manner:

A solution containing 4-methylimidazole (16.4 g), N,N-dimethylcarbamoyl chloride (30 g) and triethylamine (30 g) in acetonitrile (125 mL) is stirred at reflux for 20 hours. Upon cooling, the reaction is diluted with diethyl ether (1000 mL) and then filtered. The filtrate is concentrated and the residue is distilled under reduced pressure. 1-(Dimethylcarbamoyl)-4-methylimidazole is obtained as a colorless liquid, b.p. 104°–106° at 0.35 mm Hg.

EXAMPLE 11 a) A solution of n-butyl lithium (25 mL of 2.1 M reagent in hexane, 0.0525 mole) is added dropwise in an N$_2$ atmosphere to a solution of di-isopropylamine (5.6 g) in tetrahydrofuran (100 mL) which is maintained at −20°. This cold solution is then added dropwise to a solution of 4-(1-imidazolylmethyl)benzonitrile (9.15 g) in tetrahydrofuran (250 mL) which is maintained at −50° during addition and for 30 minutes subsequently. The reaction mixture is then cooled to −70° and methyl iodide (10.7 g) is added, all at once. The reaction is stirred at −70° for 30 minutes and then without external cooling for 10 hours. The reaction is quenched by addition of water (300 mL) and extracted with diethyl ether (3×100 mL). The combined ether extracts are extracted with 3 N hydrochloric acid (3×60 mL) and the acid extracts are made basic (pH 9) with 6 N sodium hydroxide. The crude product is extracted into ether (3×60 mL), and after drying (MgSO$_4$) and solvent evaporation, 4-[1-(1-imidazolyl)ethyl]benzonitrile is obtained. The crude material is dissolved in acetone and treated with ethereal HCl to afford the hydrochloride salt, m.p. 184°–186°.

Similarly prepared are:

b) 4-[2-(1-imidazolyl)propyl]benzonitrile hydrochloride, m.p. 219°–221°;

c) 4-(alpha-n-butyl-1-imidazolylmethyl)-benzonitrile oxalate, m.p. 73°–75°;

d) 4-(alpha-isopropyl-1-imidazolylmethyl)-benzonitrile, m.p. 94°–95°;

e) 4-(alpha-benzyl-1-imidazolylmethyl)benzonitrile hydrochloride, m.p. 221°–223°;

f) 4-[alpha-(4-cyanobenzyl)-1-imidazolylmethyl]benzonitrile, m.p. 199°–201°;

EXAMPLE 12

The lithium salt of 10.0 g of 4-(1-imidazolylmethyl)-benzonitrile is prepared in THF (250 mL) in the manner described in Example 11. This solution is cooled to −60° and solid paraformaldehyde (10.0 g, previously dried for 15 hours in vacuo at 60°) is added, all at once. The reaction mixture is stirred at −60° for 1 hour and then without cooling for a further 15 hours. The reaction is then quenched with water (200 mL) and worked up in the manner described in Example 11 to afford a mixture of 4-( alpha-hydroxymethyl-1-imidazolylmethyl) benzonitrile and 4-(alpha-methylene-1-imidazolylmethyl)benzonitrile which is chromatographed on silica gel (250 g). Elution with a mixture of methylene chloride and isopropanol (19:1) affords 4-(alpha-methylene-1-imidazolylmethyl) benzonitrile. This compound forms a hydrochloride salt, m.p. 195°–197° when its solution in acetone is treated with ethereal HCl.

EXAMPLE 13 a) Racemic 4-[1-(1-imidazolyl)ethyl]benzonitrile (3.5 g) is dissolved in warm acetone (50 mL) and added to a solution of l-tartaric acid (1.2 g) in warm acetone (300 mL). The mixture is allowed to stand at room temperature overnight and the tartrate salt is collected. This material is recrystallized four times from minimal volumes of anhydrous ethanol and the resultant material is converted to the free base by dissolution in water, making basic (pH 9) with dilute sodium hydroxide and isolating (-)-4-[1-(1-imidazolyl)ethyl]benzonitrile which has an optical rotation $[alpha]D^{25} = -4.94°$.

b) (+)-4-[1-(1-Imidazolyl)ethyl]benzonitrile is obtained in a similar manner using d-tartaric acid and has an optical rotation $[alpha]D^{25} = 4.89°$.

Each enantiomer forms a hydrochloride salt, m.p. 190°–191°, when a solution in acetone is treated with ethereal HCl.

EXAMPLE 14

A solution of potassium tert-butoxide (1.10 g) in tetrahydrofuran (50 mL) is added dropwise to a solution of 4-[1-(1-imidazolyl)-5-chloropentyl]benzonitrile (2.50 g) in tetrahydrofuran at 0° (ice-bath). The reaction is allowed to proceed at 0° for 30 minutes and is then allowed to warm to room temperature during 3 hours. The reaction is then quenched with water (100 mL) and the mixture is subsequently extracted with ethyl acetate (100 mL). The organic extract is extracted with 3 N hydrochloric acid (3×30 mL) and the combined acid extracts are made basic with 6 N sodium hydroxide. The crude product is extracted into ethyl acetate (3×30 mL) and the combined extracts are dried (MgSO₄) and evaporated to afford 1-(4-cyanophenyl) -1-(1-imidazolyl)cyclopentane as an oil. The compound is dissolved in acetone and treated with ethereal HCl to afford the hydrochloride salt, m.p. 217°–219°.

The starting material, 4-[1-(1-imidazolyl)-5-chloropentyl]benzonitrile is prepared as follows:

The lithium salt of 4-[1-imidazolylmethyl]-benzonitrile (3.7 g) is prepared at −50° in tetrahydrofuran (100 mL) as described in Example 11 and the cold solution is then added dropwise to a solution of 1-chloro-4-iodobutane (8.7 g) in tetrahydrofuran (60 mL) at −60°. The reaction is maintained at −60° for 2 hours and is then quenched by addition of water (150 mL). The product is extracted as described in Example 11 and the chloropentyl intermediate is obtained as an oil. The methine-CH (triplet) is observed at 4.77 ppm in the NMR spectrum. The material is used without further purification.

EXAMPLE 15

A solution of potassium tert-butoxide (4.5 g) in tetrahydrofuran (125 mL) is added dropwise during 1 hour to a solution of 4-[1-imidazolylmethyl]benzonitrile (3.66 g) and alpha,alpha'-dichloro-o-xylene (3.50 g) in tetrahydrofuran (100 mL) which is maintained at 0° (icebath). The reaction mixture is subsequently stirred for a further 1 hour without external cooling and is then quenched with water (200 mL) and extracted with ethyl acetate (150 mL). The organic extracts are then extracted with 3 N hydrochloric acid (3×80 mL) and the acidic extracts are made basic with 6 N sodium hydroxide and the crude product is extracted into ethyl acetate (3×50 mL). The material obtained after drying (MgSO₄) and solvent evaporation is chromatographed on silica gel (100 g). Elution with ethyl acetate affords the crystalline 2-(4-cyanophenyl)-2-(1-imidazolyl) indane which is recrystallized from isopropanol, m.p. 150°–152°.

EXAMPLE 16 a) The lithium salt of 4-[1-imidazolylmethyl]benzonitrile (3.7 g) is prepared at −50° in tetrahydrofuran (100 mL) in the manner described in Example 11. This cold solution is then added dropwise to a solution of diphenyl disulfide (6.5 g) in tetrahydrofuran (100 mL) at −50°. The reaction mixture is stirred for 2 hours, then quenched by addition of water (150 mL) and worked up as described in Example 11 to afford 4-[alpha-phenylthio-1-imidazolylmethyl]benzonitrile as an oil. The compound forms a hydrochloride salt, m.p. 159°–162° when its solution in ether is treated with ethereal HCl.

b) 4- [alpha-methylthio-1-imidazolylmethyl]benzonitrile hydrochloride, m.p. 137°–140° is similarly prepared.

EXAMPLE 17

2,2-Bis-(4-methoxyphenyl) -2-hydroxy-1-(1-imidazolyl)-1-(4-cyanophenyl)-ethane (10.2 g) is dissolved in thionyl chloride (25 mL) and the solution is stirred at room temperature for 36 hours. The solvent is evaporated and the residue is chromatographed on silica gel (250 g). Elution with ethyl acetate affords the crystalline 2,2-bis- (4-methoxyphenyl) -1-(1-imidazolyl) -1-(4-cyanophenyl)-ethylene. The compound has m.p. 174°–176° after recrystallization from isopropanol.

The starting material is prepared as follows:

The lithium salt of 4-(1-imidazolylmethyl)benzonitrile (5.5 g) is prepared in tetrahydrofuran (200 mL) in the manner described in Example 11. This cold solution is added dropwise to a solution of 4,4'-dimethoxybenzophenone (7.5 g) in tetrahydrofuran (100 mL) at −60°. The reaction is allowed to proceed for 4 hours at −60° and is then quenched by dropwise addition of acetic acid (0.5 mL) and then water (200 mL). After warming to room temperature, the mixture is diluted with ether (200 mL). The separated organic phase is washed with water (3×50 mL), dried over MgSO₄ and, after evaporating the solvents, the residue is chromatographed on silica gel (200 g). Elution with ethyl acetate affords 2,2-bis-(4-methoxyphenyl) -2-hydroxy-1-(1-imidazolyl)-1-(4-cyanophenyl)-ethane as a foam (NMR, CH-methine 4.15 ppm).

EXAMPLE 18

Treatment of 2,2-bis-(4-methoxyphenyl) -1-(1-imidazolyl)-1-(4-cyanophenyl)-ethylene with boron tribromide using procedure analogous to that described in Example 7 yields 2,2-bis-(4-hydroxyphenyl)-1-(1-imidazolyl)-1-(4-cyanophenyl)-ethylene hydrobromide, m.p. 178° dec.

EXAMPLE 19 a) Zinc dust (23 g) is added in small portions over 15 minutes to a solution of 4-(alpha-chloro-3-pyridylmethyl)benzonitrile hydrochloride (13.25 g) in a mixture of acetic acid (110 mL) and water (5 mL). The reaction is stirred at room temperature for 3 hours and is then filtered through a pad of Celite. The filtrate is concentrated and the residue is taken up in ether (250 mL) and washed with 3 N sodium hydroxide (3×100 mL) and brine. After drying the ethereal solution (anhydrous $Na_2SO_4$), solvent evaporation affords crude 4-(3-pyridylmethyl)-benzonitrile. The compound forms a hydrochloride salt, m.p. 155°–157° when its solution in ethyl acetate is treated with ethereal HCl.

The starting material is prepared from (3-pyridyl)-(4'-N-tert-butylcarbamoylphenyl)-methanol by treatment with thionyl chloride as described in Example 3.

(3-Pyridyl)-(4'-N-tert-butylcarbamoylphenyl)-methanol is prepared from N-tert-butyl-4-bromobenzamide and 3-pyridinecarboxaldehyde (see Example 3).

Similarly prepared are:

b) 4-[alpha-(3-pyridyl)-3'-pyridylmethyl]benzonitrile, m.p. 125°–127°;

c) 4-[alpha-(4-pyridyl)-3'-pyridylmethyl]benzonitrile oxalate, m.p. 172°–174°.

EXAMPLE 20 a) 4-[1-(1,2,4-Triazolyl)-methyl]-benzonitrile is reacted with potassium tert-butoxide and 4-fluorobenzonitrile according to procedure in Example 2 to yield [alpha-(4-cyanophenyl) -1-(1,2,4-triazolyl)-methyl]benzonitrile, m.p. 181°–183°.

b) 4-[1-(1,3,4-Triazolyl)-methyl]-benzonitrile is similarly reacted with 4-fluorobenzonitrile to yield 4-[alpha-(4-cyanophenyl)-1-(1,3,4-triazolyl)-methyl ]benzonitrile, m.p. 239°–243°.

EXAMPLE 21

4-(3-Pyridylmethyl)-benzonitrile is reacted with potassium tert-butoxide and 4-fluorobenzonitrile according to the procedure in Example 2 to yield 4-[alpha(4-cyanophenyl)-3-pyridylmethyl]-benzonitrile hydrochloride, m.p. 120°–125° dec.

EXAMPLE 22

To 48.0 L of acetone under nitrogen is added 4.326 Kg of potassium carbonate, 0.26 Kg of potassium iodide, 3.2 Kg of imidazole and 4.745 Kg of alpha-chloro-4-tolunitrile. The mixture is stirred at 45° under nitrogen for 26 hours. The reaction is cooled, filtered and the solvent is evaporated at reduced pressure. The residue is redissolved in 40 L of methylene chloride, washed with 40 L of water and twice with 10 L of water. The organic phase is dried over magnesium sulfate and evaporated to yield the crude product which is stirred with 6.4 L of ether for 2 hours. The solid is filtered, washed with 9 L of ether and dried at 40° and 20 mm Hg for 17 hours to yield 4-(1-imidazolylmethyl)-benzonitrile, the compound of Example 1.

EXAMPLE 23

In portions of approximately 500 g, 4.44 Kg of potassium tert-butoxide is added to 25 L of dimethylformamide, precooled to −10°, without allowing the solvent temperature to rise above −4°. The solution is recooled to −8° and a solution of 3.3 Kg 4-(1-imidazolylmethyl)-benzonitrile in 12.5 L of dimethylformamide is added within 3.3 hours. The rate of addition is adjusted to maintain the reaction temperature at −7±2°.

The solution is stirred for 45 minutes while cooling to −11° and a solution of 2.18 Kg of para-fluorobenzonitrile in 5 L of dimethylformamide is added over 3.5 hours. The reaction temperature is maintained at 3±4°. After 1.25 hours, the pH of the reaction is brought to 7 with 3.0 L of concentrated hydrochloric acid, stirred an additional 20 minutes and allowed to stand overnight. The solvent is removed by distillation at 8 mm Hg over 7 hours. The resulting oil is partitioned between 25 L of methylene chloride and 35 L of water. The layers are separated. The aqueous phase is extracted with 7 L of methylene chloride and the combined organic phases are washed with 10 L of $H_2O$ and twice with 1.1 L of 3 N hydrochloric acid. The combined acidic layers are washed with 7 L of methylene chloride and added to a mixture of 10 Kg of ice and 20 L of methylene chloride. The solution is stirred and brought to pH 11 with 2.8 L of concentrated sodium hydroxide. The aqueous layer is separated and extracted with 5 L of methylene chloride. The combined organic phases are washed with 10 L of water and dried over magnesium sulfate. Filtration and evaporation at 45° and 8 mm Hg, yields 4-[alpha-(4-cyanophenyl)-1-imidazolylmethyl]-benzonitrile as an oil; IR $(CH_2Cl_2)$2240 $cm^{-1}$.

A solution of 9.23 Kg of the above free base in 19.1 L of isopropanol is treated with 0.45 Kg of decolorizing carbon and after 15 minutes is filtered into a stirred solution of 1.84 Kg of succinic acid in 31.4 L of isopropanol at 50°. The solution is stirred for 14 hours at 50° and allowed to cool to room temperature. The resulting crystalline solid is collected by filtration, washed with 8 L of isopropanol and 5 L of diethyl ether and dried at 90° and 20 mm Hg for 28 hours to yield 4-[alpha-(4-cyanophenyl) -1-imidazolylmethyl ]benzonitrile hemisuccinate, m.p. 149°–150°. Recrystallization from isopropanol/ether gives product melting at 151°–152°.

EXAMPLE 24

To a solution of 39.2 g of alpha-bromo-p-tolunitrile in 1 L of acetone are added sequentially 20.72 g of 1,2,4-triazole, 27.8 g of potassium carbonate and 1.7 g of potassium iodide. The reaction is stirred for 8 hours at 55° under argon, cooled to room temperature, filtered and evaporated. The residue is partitioned between methylene chloride and water. The organic phase is separated, washed with brine, dried over sodium sulfate and evaporated. The resulting crystalline crude product is chromatographed on 300 g of silica with toluene and ethyl acetate (1:1 to 0:1) to yield 4-[1-(1,2,4-triazolyl) methyl] benzonitrile (see example 9).

EXAMPLE 25

(a) To a stirring solution of potassium tert-butoxide (4.8 g) in 40 mL of dimethylformamide is added dropwise a solution of 4-[1-(1,2,4-triazolyl)methyl]benzonitrile (3.7 g) in 40 mL of dimethylformamide. The mixture is stirred for 30 minutes and a solution of 4-fluorobenzonitrile (2.7 g) in 20 mL of dimethylformamide is added dropwise. After 30 minutes, the reaction is quenched with saturated aqueous ammonium chloride and the mixture is evaporated to dryness. The residue is diluted with water and extracted three times with ethyl acetate. The combined extracts are washed twice with water, and once with saturated brine solution. The ethyl acetate extract is dried over magnesium sulfate and evaporated to dryness. The residue is triturated with ether and then recrystallized from 95% ethanol to yield 4-[alpha(-(4-cyanophenyl)-1-(1,2,4-triazolyl)-methyl]-benzonitrile, m.p. 181°–183°.

(b) Using 4-[1-(1,3,4-triazolyl)methyl]-benzonitrile as starting material in the above procedure, 4- 8 alpha-(4-cyanophenyl)-1-(1,3,4-triazolyl)methyl]benzonitrile, m.p. 239°–243°, is obtained.

EXAMPLE 26

A solution of 46 g of 4-[1-(1,2,4-triazolyl)-methyl]-benzonitrile in 350 ml of dimethylformamide is slowly added with external cooling to 77 g of potassium tert-butoxide in 250 ml of dimethylformamide, so that the temperature stays between 24 and 26°. After 45 minutes, a solution of 37.75 g of 4-fluorobenzonitrile in 250 mL of dimethylformamide is added. The reaction mixture is stirred an additional 30 minutes at room temperature, diluted with 100 mL of methylene chloride, cooled to 0°, brought to pH 7.3 with concentrated HCl and evaporated. The residue is partitioned between methylene chloride and water. The organic phase is separated, washed with brine dried over sodium sulfate and evaporated. The resulting crude product is recrystallized from ether/ethyl acetate to yield 4-[alpha-(4-cyanophenyl)-1-(1,2,4-triazolyl) methyl]-benzonitrile, m.p. 184°–185°.

EXAMPLE 27

The following compounds are prepared according to methodology described in Examples 25 and 26.

(a) 4-[1-(1,2,4-triazolyl)-methyl]-benzonitrile is reacted with 4-bromofluorobenzene to yield 4-[alpha-(4-bromopheny l)-1-(1,2,4-triazolyl)-methyl]-benzonitrile.

(b) 4-[1-(1,3,4-triazolyl)-methyl]-benzonitrile is reacted with 2-fluorobenzonitrile to yield 4-[alpha-(2-cyanophenyl)-1-(1,3,4-triazolyl)-methyl]-benzonitrile.

(c) 4-[1-(1,2,4-triazolyl)-methyl]-benzonitrile is reacted with 4-(trifluoromethyl)-fluorobenzene to yield 4-[alpha-(4-trifluoromethylphenyl)-1-(1,2,4-triazolyl)-methyl]-benzonitrile.

EXAMPLE 28

1,2,4-Triazole (9.5 g) and 4-(alpha-chloro-4'-cyanobenzyl)-benzonitrile (11.6 g) are intimately mixed and heated together in an oil bath at 110°–120° for 15 hours. The reaction mixture is diluted with water (200 mL) and extracted with ethyl acetate (3×75 mL). The remainder of the work-up is carried out as described in Example 9, yielding 4-[alpha-(4-cyanophenyl)-1-(1,2,4-triazolyl)methyl]-benzonitrile, and 4-[alpha-(4-cyanophenyl)-1-(1,3,4-triazolyl)-methyl]benzonitrile.

EXAMPLE 29

A solution of 4-(alpha-chloro-4'-cyanobenzyl)-benzonitrile (20.2 g) and 1,2,4-triazole (16.5 g) in dimethylformamide (130 mL) is stirred and heated at 160° for 2 hours. The reaction is cooled, diluted with water (800 mL) and extracted into ethyl acetate (3×150 mL) The remainder of the work-up is carried out in the manner described in Example 9 to yield 4-[alpha-(4-cyanophenyl)-1-(1,2,4-triazolyl)methyl]-benzonitrile and 4-[alpha-(4-cyanophenyl)-1-(1,3,4-triazolyl)methyl]benzonitrile.

The starting material, 4-(alpha-chloro-4'-cyanobenzyl)-benzonitrile is prepared as described in Example 3.

EXAMPLE 30

The following compounds are prepared according to the methods described in examples 28 and 29.

(a) 1,2,4-Triazole is reacted with 4-(alpha-chloro-4'-bromobenzyl)benzonitrile to yield 4-[alpha-(4-bromophenyl)-1-(1,2,4-triazolyl)methyl]benzonitrile and 4-[alpha-(4-bromophenyl)-1-(1,3,4-triazolyl)methyl]benzonitrile.

(b) 1,2,4-Triazole is reacted with 2-(alpha-chloro-4'-chlorobenzyl)benzonitrile to yield 2-[alpha-(4-chlorophenyl)-1-(1,2,4-triazolyl)methyl]-benzonitrile and 2-[alpha-(4-chlorophenyl)-1-(1,3,4-triazolyl)methyl]benzonitrile.

(c) 1,2,4-Triazole is reacted with 4-(alpha-chloro-4'-bromobenzyl)benzonitrile to yield 2-[alpha-(4-bromophenyl)-1-(1,2,4-triazolyl)methyl]benzonitrile and 2-[alpha-(4-bromophenyl)-1-(1,3,4-triazolyl)methyl]benzonitrile.

(d) 1,2,4-Triazole is reacted with 4-(alpha-chloro-4'-methoxybenzyl)benzonitrile to yield 4-[alpha-(4-methoxyphenyl)-1-(1,2,4-triazolyl)methyl]benzonitrile and 4-[alpha-(4-methoxyphenyl)-1-(1,3,4-triazolyl)methyl]benzonitrile.

(e) 1,2,4-Triazole is reacted with 4-(alpha-chloro-2'-methoxybenzyl)benzonitrile to yield 4-[alpha-(2-methoxyphenyl-1-(1,2,4-triazolyl)methyl]benzonitrile and 4-[alpha-(2-methoxyphenyl)-1-(1,3,4-triazolyl)methyl]benzonitrile.

(f) 1,2,4-Triazole is reacted with 4-[alpha-chloro-(3'-pyridyl)methyl]benzonitrile to yield 4-[alpha-(3-pyridyl)-1-(1,2,4-triazolyl)methyl]benzonitrile and 4-[alpha-(3-pyridyl)-1-(1,3,4-triazolyl)methyl]-benzonitrile.

(g) 1,2,4-Triazole is reacted with 4-[alpha-chloro-(2-thienyl)methyl]benzonitrile to yield 4-[alpha-(2-thienyl)-1-(1,2,4-triazolyl)methyl]benzonitrile and 4-[alpha-(2-thienyl)-1-(1,3,4-triazolyl)methyl]benzonitrile.

(h) 1,2,4-Triazole is reacted with 4-[alpha-chloro-(3-thienyl)methyl]benzonitrile to yield 4-[alpha-(3-thienyl)-1-(1,2,4-triazolyl)methyl]benzonitrile and 4-[alpha-(3-thienyl)-1-(1,3,4-triazolyl)methyl]-benzonitrile.

(i) 1,2,4-Triazole is reacted with 4-(alpha-chlorobenzyl)benzonitrile to yield 4-[alpha-phenyl)-1-(1,2,4-triazolyl)methyl]benzonitrile and 4-[alpha-phenyl)-1-(1,3,4-triazolyl)methyl]benzonitrile.

(j) 1,2,4-Triazole is reacted with 4-[alpha-chloro-(p-tolyl)methyl]benzonitrile to yield 4-[alpha-(p-tolyl)-1-(1,2,4-triazolyl)methyl]benzonitrile and 4-[alpha-(p-tolyl)-1-(1,3,4-triazolyl)methyl]benzonitrile.

(k) 1,2,4-Triazole is reacted with 3-(alpha-chlorobenzyl)benzonitrile to yield 3-[(alpha-phenyl)-1-(1,2,4-triazolyl)methyl]benzonitrile and 3-[(alpha-phenyl)-1-(1,3,4-triazolyl)methyl]benzonitrile.

The starting alpha-chloro compounds are prepared as generally described in Examples 3 and 5.

EXAMPLE 31

(a) Using procedure essentially as described in Example 6, 4-[alpha-(4-cyanophenyl)-1-(1,2,4-triazolyl)methyl]benzonitrile is treated with methyl iodide to obtain 4-[alpha-(4-cyanophenyl)-alpha-methyl-1-(1,2,4-triazolyl)methyl]benzonitrile.

(b) 4-[alpha-(4-cyanophenyl)-alpha-methyl-1-(1,3,4-triazolyl)methyl]benzonitrile is similarly prepared.

EXAMPLE 32

(a) Using procedure in Example 7, 4-[alpha-(4-methoxyphenyl)-1-(1,2,4-triazolyl)methyl]benzonitrile is converted to 4-[alpha-(4-hydroxyphenyl)-1-(1,2,4-triazolyl)methyl]-benzonitrile.

(b) 4-[alpha-(2-hydroxyphenyl)-1-(1,2,4-triazolyl)methyl]benzonitrile is similarly prepared.

(c) 4-[alpha-(4-hydroxybenzyl)-1-(1,2,4-triazolyl)methyl]benzonitrile, is also similarly prepared.

EXAMPLE 33

Using procedure described in Example 8, 2-[alpha-phenyl-1-(1,2,4-triazolyl)methyl]-benzonitrile is prepared from 2-[alpha-(4-bromophenyl)-1-(1,2,4-triazolyl)methyl]benzonitrile.

EXAMPLE 34

(a) A solution of n-butyl lithium (25 mL of 2.1 M reagent in hexane, 0.0525 mole) is added dropwise in an $N_2$ atmosphere to a solution of di-isopropylamine (5.6 g) in tetrahydrofuran (100 mL) which is maintained at −20°. This cold solution is then added dropwise to a solution of 4-[1-(1,2,4-triazolylmethyl)benzonitrile (9.10 g) in tetrahydrofuran (250 mL) which is maintained at −50° during addition and for 30 minutes subsequently. The reaction mixture is then cooled to −70° and 7.1 g (3.1 mL) of methyl iodide is added dropwise. The reaction is stirred at −70° for 30 minutes and then without external cooling for 10 hours. The reaction is quenched by addition of water (300 mL) and extracted with diethyl ether (3×100 mL). The combined ether extracts are extracted with 3 N hydrochloric acid (3×60 mL) and the acid extracts are made basic (pH 9) with 6 N sodium hydroxide. The crude product is extracted into ether (3×60 mL), and after drying (MgSO$_4$) and solvent evaporation, 4-[1-(1-(1,2,4-triazolyl)ethyl]benzonitrile is obtained.

The following compounds are similarly prepared as follows:

(b) 4-[1-(1-(1,2,4-triazolyl))ethyl]benzonitrile (9.35 g) is reacted with 7.1 g of methyl iodide to yield 4-[alpha,alpha-dimethyl-(1-(1,2,4-triazolyl))-methyl]benzonitrile.

(c) 4-[1-(1-(1,2,4-triazolyl))methyl]benzonitrile (9.10 g) is reacted with 8.5 g of 2-iodopropane to yield 4-[alpha-isopropyl-1-(1,2,4-triazolyl)methyl]benzonitrile.

(d) 4-[1-(1-(1,2,4-triazolyl))methyl]benzonitrile (9.10 g) is reacted with 8.55 g of benzyl bromide to yield 4-[alpha-benzyl-1-(1,2,4-triazolyl)methyl]benzonitrile.

(e) 4-[1-(1-(1,2,4-triazolyl))methyl]benzonitrile (9.10 g) is reacted with 6.85 g of n-butyl bromide to yield 4-[alpha-n-butyl-1-(1,2,4-triazolyl)methyl]benzonitrile.

(f) 4-[1-(1-(1,2,4-triazolyl))methyl]benzonitrile (9.10 g) is reacted with 9.7 g of alpha-bromo-p-tolunitrile to yield 4-[alpha-(4-cyanobenzyl-1-(1,2,4-triazolyl)methyl]benzonitrile.

EXAMPLE 35

The lithium salt of 10.0 g of 4-(1-(1,2,4-triazolyl)methyl)-benzonitrile is prepared in THF (250 mL) in the manner described in Example 34. This solution is cooled to −60° and solid paraformaldehyde (10.0 g, previously dried for 15 hours in vacuo at 60°) is added, all at once. The reaction mixture is stirred at −60° for 1 hour and then without cooling for a further 15 hours. The reaction is then quenched with water (200 mL) and worked up in the manner described in Example 34 to afford a mixture of 4-(alpha-hydroxymethyl-1-(1,2,4-triazolyl)methyl)benzonitrile and 4-(alpha-methylene-1-(1,2,4-triazolyl)-methyl)benzonitrile which is chromatographed on silica gel to afford 4-(alpha-methylene-1-(1,2,4-triazolyl)-methyl) benzonitrile.

EXAMPLE 36

A solution of potassium tert-butoxide (1.10 g) in tetrahydrofuran (50 mL) is added dropwise to a solution of 4-[1-(1,2,4-triazolyl) -5-chloropentyl]benzonitrile (2.50 g) in tetrahydrofuran at 0° (ice-bath). The reaction is allowed to proceed at 0° for 30 minutes and is then allowed to warm to room temperature during 3 hours. The reaction is then quenched with water (100 mL) and the mixture is subsequently extracted with ethyl acetate (100 mL). The organic extract is extracted with 3 N hydrochloric acid (3×30 mL) and the combined acid extracts are made basic with 6 N sodium hydroxide. The crude product is extracted into ethyl acetate (3×30 mL) and the combined extracts are dried (MgSO$_4$) and evaporated to afford 1-(4-cyanophenyl)-1-(1,2,4-triazolyl)cyclopentane. The compound is dissolved in acetone and treated with ethereal HCl to afford the hydrochloride salt.

The starting material, 4-[1-(1,2,4-triazolyl)-5-chloropentyl]benzonitrile is prepared as follows:

The lithium salt derived from 3.7 g of 4-[1,2,4-triazolylmethyl]-benzonitrile is prepared as described in Example 34, and the cold solution is then added dropwise to a solution of 1-chloro-4-iodobutane (8.7 g) in tetrahydrofuran (60 mL) at 60°. The reaction is maintained at −60° for 2 hours and is then quenched by addition of water (150 mL). The product is isolated by extraction and used without further purification.

EXAMPLE 37

A solution of potassium tert-butoxide (4.5 g) in tetrahydrofuran (125 mL) is added dropwise during 1 hour to a solution of 4-[1-(1,2,4-triazolyl)-methyl]benzonitrile (3.68 g) and alpha,alpha'-dichloro-o-xylene (3.50 g) in tetrahydrofuran (100 mL) which is maintained at 0° (ice-bath). The reaction mixture is subsequently stirred for a further 1 hour without external cooling and is then quenched with water (200 mL) and extracted with ethyl acetate (150 mL). The organic extracts are then extracted with 3 N hydrochloric acid (3×80 mL) and the acidic extracts are made basic with 6 N sodium hydroxide and the crude product is extracted into ethyl acetate (3×50 mL). The material obtained after drying (MgSO$_4$) and solvent evaporation is chromatographed on silica gel (100 g). Elution with ethyl acetate affords 2-(4-cyanophenyl)-2-[1-(1,2,4-triazolyl)]indane.

EXAMPLE 38

(a) The lithium salt of 4-[1-(1,2,4-triazolyl)methyl]benzonitrile (3.7 g) is prepared at −50° in tetrahydrofuran (100 mL) in the manner described in Example 34. This cold solution is then added dropwise to a solution of diphenyl disulfide (6.5 g) in tetrahydrofuran (100 mL) at −50°. The reaction mixture is stirred for 2 hours, then quenched by addition of water (150 mL) and worked up as described in Example 34 to afford 4-[alphaphenylthio-1-(1,2,4-tri azolyl)methyl]-benzonitrile.

(b) 4-[alpha-Methylthio-1-(1,2,4-triazolyl)methyl]benzonitrile is similarly prepared.

EXAMPLE 39

Racemic 4-[1-(1,2,4-triazolyl)-ethyl]benzonitrile is treated essentially as described in Example 13 with l-tartaric acid or d-tartaric acid to obtain the optical antipodes (-)4-[1-(1,2,4-triazolyl)-ethyl]benzonitrile and (+) 4-[1-(1,2,4-triazolyl)-ethyl]benzonitrile.

EXAMPLE 40

The following compounds are prepared according to methodology described in the previous examples.

(a) 4-(3-pyridylmethyl)-benzonitrile is reacted with 4-bromofluorobenzene to yield 4-[alpha-(4-bromophenyl)-3-pyridylmethyl]-benzonitrile.

(b) 4-(3-pyridylmethyl)-benzonitrile is reacted with 2-fluorobenzonitrile to yield 4-[alpha-(2-cyanophenyl)-3-pyridylmethyl]-benzonitrile.

(c) 4-[3-pyridylmethyl]-benzonitrile is reacted with 4-(trifluoromethyl)-fluorobenzene to yield 4-[alpha-(4-trifluoromethylphenyl)-3-pyridylmethyl]benzonitrile.

EXAMPLE 41

(a) Using methodology described e.g. in example 34, 4-(3-pyridylmethyl)-benzonitrile is reacted with methyl iodide to obtain 4-[1-(3-pyridyl)-ethyl]-benzonitrile.

(b) Similarly 4-[1-(3-pyridyl)-ethyl]-benzonitrile is again reacted with methyl iodide to obtain 4-(alpha,alpha-dimethyl-3-pyridylmethyl)-benzonitrile.

(c) Similarly 4-(3-pyridylmethyl)-benzonitrile is reacted with alpha-bromo-p-tolunitrile to yield 4-[alpha-(4-cyanobenzyl)-3-pyridylmethyl]-benzonitrile.

EXAMPLE 42

Using procedure as described in the previous examples, 4-[alpha-(4-cyanophenyl)-3-pyridylmethyl]benzonitrile is reacted with methyl iodide to obtain 4-[alpha-(4-cyanophenyl)-alpha-methyl-3-pyridylmethyl]-benzonitrile.

EXAMPLE 43

Using procedure described in Example 36, the lithium salt of 4-(3-pyridylmethyl)-benzonitrile is treated with 1-chloro-4-iodobutane and the intermediate cyclized to obtain 1-(4-cyanophenyl)-1-(3-pyridyl)-cyclopentane.

EXAMPLE 44

A suspension of potassium tert-butoxide (2.0 g) in dimethylformamide (15 mL) is stirred and cooled to −10° (ice-salt bath), and a solution of 4-(3-pyridylmethyl)benzonitrile (1.55 g) in dimethylformamide (10 mL) is added so that the reaction temperature remains below 0°. The resulting solution is stirred at 0° for 0.5 hour and then a solution of 4-fluorobenzonitrile (1.1 g) in dimethylformamide (10 mL) is added while keeping reaction temperature below 5°. The reaction mixture is stirred at room temperature overnight, treated with saturated aqueous ammonium chloride and evaporated to dryness. The residue is diluted with water and the crude product is extracted 3 times with 3 N hydrochloric acid and, after washing the acid extracts with ether, the solution is made basic with dilute sodium hydroxide and the product is again extracted into ethyl acetate. The combined extracts are dried (MgSO4), evaporated to give crude oil which is purified by chromatography on silica gel using methylene chloride:methanol (100:2) as eluent to yield 4-[alpha-(4-cyanophenyl)-3-pyridylmethyl]-benzonitrile which is converted to the hydrochloride salt in ether, m.p. 120°–125° dec., the compound of Example 21.

EXAMPLE 45

To a mixture of 148.5 g of 4-[alpha-chloro-(3-pyridylmethyl) ]benzonitrile and 560 ml of 1,3-dimethyl-3, 4,5, 6-tetrahydro-2 (1H)-pyrimidone under an argon atmosphere 190 ml of N,N-diisopropyl-ethyl-amine are added at room temperature. The clear solution is cooled to 20° C. and while stirring 66.7 g of imidazole are added. Then the mixture is heated to 140° C. The reaction mixture is concentrated in vacuo at 90° C. and the residue is dissolved in 2.5 l of ethyl acetate. Then 1 l of an ammonia solution is added and the mixture is extracted three times with 0.5 l of 2 N ammonia and once with 0.5 l of brine. The organic layers are dried, filtered and concentrated under reduced pressure. The residue is evaporated at 60° C. under high vacuum and then chromatographed on silica gel. Eluation with methylene chloride/methanol 95:5, for example, yields 4-[alpha-(3-pyridyl)-1-imidazolylmethyl]benzonitrile, IR(CN): 2237 cm$^{-1}$; M/e: 260.

The starting material can be prepared, for example, as follows:

A mixture of 22.5 l of methylene chloride and 3030 ml of tert-butylamine is cooled to 0° C. Then a solution of 3 kg of 4-bromo-benzoyl chloride in 15 l of methylene chloride is added in portions. The mixture is cooled to 0°–5° C. and then stirred over night at room temperature. The reaction mixture is filtered and the filtrate washed with 5 l of methylene chloride, three times with 5 l of 3 N HCl, twice with 4 l of NaHCO3 and twice with 2 l of brine. The organic layer is dried over Na2SO4 and evaporated. The crude crystals are stirred with 8 l of ether for 30 minutes and the mixture is cooled to 0° C. and filtered. Thus 4-bromo-N-tert-butyl-benzamide is obtained in form of white crystals, m.p.133°–134° C.

A solution of 256.2 g of 4-bromo-N-tert-butyl-benzamide in 4.4 l of tetrahydrofuran is cooled to −78° C. and under an argon atmosphere 1.3 l of n-butyl lithium in hexane (1.6 moles) are added slowly while stirring. Then first a solution of 93.8 ml of pyridin-3-carboxaldehyde in 440 ml of tetrahydrofuran are added and after the reaction is finished 1 l of a saturated ammonium chloride solution is added. The temperature is allowed to go up to +5° C. and 1 l of ether is added. The reaction mixture is washed with 500 ml of ether and 500 ml of water. The organic layer is washed twice with 1.5 l of water and once with 1.5 l of brine. The organic layer is dried and evaporated. The residue is chromatographed over silica gel. Eluation with methylene chloride/methanol 9:1 yields 4-[alpha-hydroxy-(3-pyridylmethyl)]-N-tert-butyl-benzamide, m.p. 142°–144° C.

To 1.1 l of sulfuryl chloride a suspension of 568.8 g of 4-[alpha-hydroxy-(3-pyridylmethyl)]-N-tert-butyl-benzamide in 2.5 l of methylene chloride is added at a bath temperature of 100° C. while stirring. The solvent is distilled off. After the formation of gas is finished, the reaction product is evaporated at 40° C. Accordingly, 4-[alpha-chloro-(3-pyridyl)-methyl]benzonitrile is obtained, m.p. 162°–165° C.

EXAMPLE 46

232 g of 4-[alpha-(3-pyridyl)-1-imidazolyl-methyl]-benzonitrile are dissolved in 8 l of ethanol at 0° C. 890 ml of 2 N sulfuric acid are added in portions. The reaction product is filtered off, washed with 2 l of ethanol and then with 1 l of hexane. The residue is concentrated in vacuo, dried at 50° C. and chromatographed on silica gel. Eluation with methylene chloride/methanol/ammonia 70:5:0.1 yields the sulfate salt of 4-[alpha-(3-pyridyl)-1-imidazolylmethyl]benzonitrile, m.p. 242°–244° C.

EXAMPLE 47

Preparation of 10,000 tablets each containing 0.5 mg of the active ingredient:

| Formula: | |
|---|---|
| 4-[alpha-(4-cyanophenyl)-1-imidazolylmethyl]-benzonitrile hemisuccinate | 5.00 g |
| Lactose | 2,535.00 g |
| Corn starch | 125.00 g |
| Polyethylene glycol 6,000 | 150.00 g |
| Magnesium stearate | 40.00 g |
| Purified water | q.s. |

All the powders are passed through a screen with openings of 0.6mm. Then the drug substance, lactose, magnesium stearate and half of the starch are mixed in a suitable mixer. The other half of the starch is suspended in 65 ml of water and the suspension is added to the boiling solution of the polyethylene glycol in 260 ml of water. The paste formed is added to the powders, which are granulated, if necessary, with an additional amount of water The granulate is dried overnight at 35°, broken on a screen with 1.2 mm openings and compressed into tablets, using concave uppers bisected.

Analogously tablets are prepared containing the other compounds disclosed and exemplified herein, e.g. 4-[alpha-(4-cyanophenyl) -1-(1,2,4-triazolyl) -methyl]-benzonitrile.

EXAMPLE 48

Preparation of 1,000 capsules each containing 1.0 mg of the active ingredient:

| Formula: | |
|---|---|
| 4-[alpha-(3-pyridyl)-1-imidazolylmethyl]-benzonitrile sulfate | 1.0 g |
| Lactose | 216.0 g |
| Modified starch | 80.0 g |
| Magnesium stearate | 3.0 g |

All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 300 mg of said mixture each, using a capsule filling machine.

Analogously capsules are prepared, containing the other compounds disclosed and exemplified herein, e.g. 4-[alpha-(4-cyanophenyl)-1-(1,2,4-triazolyl)-methy]benzonitrile.

What is claimed is:

1. A method for preparing a compound of the formula

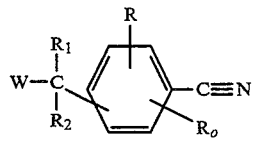

(I)

wherein R and $R_o$ represent hydrogen or lower alkyl; or R and $R_o$ located on adjacent carbon atoms and together when combined with the benzene ring to which they are attached form a naphthalene or tetrahydronaphthalene ting; $R_1$ represents hydrogen; $R_2$ represents 4-cyanophenyl; and W represents 1-(1,2,4)-triazolyl; which comprises condensing under basic conditions using an alkali metal aikoxide a compound of the formula XI

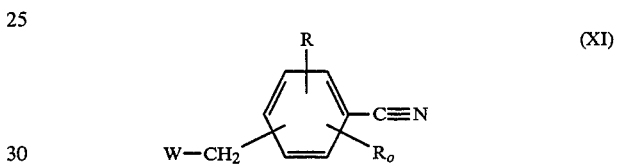

(XI)

wherein R, $R_o$ and W have meaning as defined above, with p-fluorobenzonitrile.

2. A method according to claim 1 wherein the alkali metal alkoxide is potassium t-butoxide.

3. A method according to claim 1 for preparing 4-[alpha-(4-cyanophenyl)-1-(1,2,4-triazolyl)-methyl]benzonitrile which comprises condensing 4-[1-(1,2,4)-triazolylmethyl]benzonitrile with 4-fluorobenzonitrile using potassium tert-butoxide in dimethylformamide.

4. A process according to claim 1 for preparing 4-[alpha-(4-cyanophenyl)-1-(1,2,4-triazolyl)-methyl]benzonitrile.

* * * * *